US012600748B2

(12) United States Patent
Keszey et al.

(10) Patent No.: US 12,600,748 B2
(45) Date of Patent: Apr. 14, 2026

(54) AFFINITY CHROMATOGRAPHY OF IMMUNOGLOBULINS BY USING PRE-CAPTURE FLOCCULATION

(71) Applicant: RICHTER GEDEON NYRT., Budapest (HU)

(72) Inventors: Zsuzsanna Keszey, Veszprém (HU); Zoltán Sütö, Fehérgyarmat (HU)

(73) Assignee: RICHTER GEDEON NYRT., Budapest (HU)

( * ) Notice: Subject to any disclaimer, the term of this patent is extended or adjusted under 35 U.S.C. 154(b) by 927 days.

(21) Appl. No.: 17/601,197

(22) PCT Filed: Mar. 25, 2020

(86) PCT No.: PCT/EP2020/058439
§ 371 (c)(1),
(2) Date: Oct. 4, 2021

(87) PCT Pub. No.: WO2020/200980
PCT Pub. Date: Oct. 8, 2020

(65) Prior Publication Data
US 2022/0194981 A1      Jun. 23, 2022

(30) Foreign Application Priority Data

Apr. 4, 2019    (HU) .................................... P1900112

(51) Int. Cl.
C07K 1/22          (2006.01)
C07K 1/18          (2006.01)
C07K 1/34          (2006.01)
C07K 1/36          (2006.01)

(52) U.S. Cl.
CPC .................. *C07K 1/22* (2013.01); *C07K 1/18* (2013.01); *C07K 1/34* (2013.01); *C07K 1/36* (2013.01)

(58) Field of Classification Search
CPC ... C07K 1/22; C07K 1/18; C07K 1/34; C07K 1/36
See application file for complete search history.

(56) References Cited

U.S. PATENT DOCUMENTS

2012/0282654 A1    11/2012   Yao et al.

FOREIGN PATENT DOCUMENTS

| RU | 2652911 C2 | 5/2018 |
|---|---|---|
| WO | WO 1992/16553 | 10/1992 |
| WO | WO 1992/22653 | 12/1992 |
| WO | WO 1994/11026 | 5/1994 |
| WO | WO 1995/22389 | 8/1995 |
| WO | WO 1997/29131 | 8/1997 |
| WO | WO 1998/45331 | 10/1998 |
| WO | WO 2003/002713 | 1/2003 |
| WO | WO 2007/035283 | 3/2007 |
| WO | WO 2008/091740 | 7/2008 |
| WO | WO 2008/127305 | 10/2008 |
| WO | WO 2010/151632 | 12/2010 |
| WO | WO 2011/050110 A1 | 4/2011 |
| WO | WO 2011/146394 | 11/2011 |
| WO | WO 2013/090820 | 6/2013 |
| WO | WO 2014/004281 | 1/2014 |
| WO | WO 2014/133459 | 9/2014 |
| WO | WO 2014/196926 | 12/2014 |
| WO | WO 2015/130222 | 9/2015 |
| WO | WO 2015/135884 | 9/2015 |
| WO | WO 2016/153983 | 9/2016 |
| WO | WO 2017/217930 | 12/2017 |
| WO | WO 2018-178376 A1 | 10/2018 |

OTHER PUBLICATIONS

Adaelu et al., "Development of an Alternative Monoclonal Antibody Polishing Step." BioPharm International-04-01-2012, vol. 25, Issue 5 (Year: 2012).*
Cytiva, "Optimizing elution conditions on Capto MMC using Design of Experiments" downloaded May 23, 2024 from <https://cdn.cytivalifesciences.com> (Year: 2008).*
Cytiva, "Selective removal of aggregates with Capto adhere." downloaded May 23, 2024 from <https://cdn.cytivalifesciences.com> (Year: 2007).*
Millipore Sigma, "Performing a Purification of IgG Antibodies with MabSelect Sure." downloaded May 23, 2024 from <https://www.sigmaaldrich.com> (Year: 2007).*
Del Real, "Scale-Down Characterisation of Post-Cenfrifuge Flocculation Processes and the Study of its Impact upon Downstream Processing during Mammalian Cell Antibody Production", Thesis submitted to University College London, (Dec. 1, 2016), p. 1-325.
Office Action corresponding to Japanese Patent Application No. 2021-558539 dated Feb. 1, 2023. (with Translation).

(Continued)

*Primary Examiner* — Suzanne M Noakes
*Assistant Examiner* — Ciara A McKnight
(74) *Attorney, Agent, or Firm* — Jenkins, Taylor & Hunt, P.A.

(57) ABSTRACT

The present invention relates to new methods for the purification of immunoglobulins from cell culture harvest. These methods are characterized by cleaning steps preceding an initial capture chromatography step. Preferably, the initial capture chromatography is an affinity chromatography and the pre-capture cleaning effect is obtained by flocculation and filtration. By using such pre-capture cleaning steps, an improved quality of the eluted immunoglobulin from the capture matrix is achieved. Furthermore, the enhanced clarification of the cell culture liquid results in reduced precipitations during affinity chromatography and thus increases the lifetimes of the expensive affinity resin. This is an important improvement for immunoglobulin purification in large scale production. The present invention further relates to sequential polishing chromatographies and filtration steps downstream to the capture chromatography, yielding immunoglobulins of high purity.

26 Claims, 5 Drawing Sheets

(56) References Cited

OTHER PUBLICATIONS

Office Action corresponding to Russian Patent Application No. 2021130988/04 dated Aug. 15, 2022.

Riske, F., et al., "The use of chitosan as a flocculant in mammalian cell fulture dramatically improves clarification throughput without adversely impacting monoclonal antibody recovery." Journal of Biotechnology, 2007, vol. 128, No. 4, pp. 813-823, DOI:10.1016/j.biotech.2006.12.012.

Search Report corresponding to Russian Patent Application No. 2021130988/04 dated Aug. 8, 2022.

Office Action corresponding to Hungarian Office Action Application No. P190011214 dated Jan. 16, 2023.

Del Real. Scale-Down Characterisation of Post-Centrifuge Flocculation Processes and the Study of its Impact upon Downstream Processing during Mammalian Cell Antibody Production. Thesis submitted to University College London, Dec. 1, 2016 (Dec. 1, 2016), Chapter 7, pp. 234-261.

Fahrner et al., 2001 "Industrial Purification of Pharmaceutical Antibodies: Development, Operation, and Validation of Chromatography Processes", Biotechnology and Genetic Engineering Reviews 18, 301-327.

Farid, 2009 "Economic Drivers and Trade-Offs in Antibody Purification Processes: The future of therapeutic MAbs lies in the development of economically feasible downstream processes", BioPharm Int. Supplements, Oct. 2, 2009.

Felo et al., 2015 "Industrial application of impurity flocculation to streamline antibody purification processes" Pharm. Bioprocess 3(2), 115-125.

Gagnon, 1996 "Purification Tools for Monoclonal Antibodies", Validated Biosystems, Inc., 1-253.

International Search Report corresponding to International Application No. PCT/EP2020/058439 dated Jul. 3, 2020.

Kadaji and G. V. Betageri, 2011 "Water Soluble Polymers for Pharmaceutical Applications", Polymers 3, 1972-2009.

Kang et al., 2013 "Development of a Novel and Efficient Cell Culture Flocculation Process Using a Stimulus Responsive Polymer to Streamline Antibody Purification Processes", Biotechnol. Bioeng. 110 (11), 2928-2937.

Kelly et al., 2009 "Downstream processing of monoclonal antibodies: Current practices and future opportunities", in: Process Scale Purification of Antibodies, edited by U. Gottschalk , John Wiley & Sons, Inc.

Liu, 2010 "Recovery and purification process development for monoclonal antibody production", mabs Landes Biosciences 2(5), 480-499.

Luo et al., 2017 "Liquid-liquid phase separation causes high turbidity and pressure during low pH elution process in Protein A chromatography", J. Chromatogr. A, 1488, 57-67.

McNerney et al., 2015, "PDADMAC flocculation of Chinese hamster ovary cells: Enabling a centrifuge-less harvest process for monoclonal antibodies" mAb (Amgen) 7(2), 413-427.

Shukla et al., 2005, "Strategies to Address Aggregation During Protein A Chromatography" BioProcess International, May 2005, 36-44.

Singh et al., 2016, "Clarification Technologies for Monoclonal Antibody Manufacturing Processes: Current State and Future Perspectives", Eur. J. Biochem. 192, 767-775.

Written Opinion corresponding to International Application No. PCT/EP2020/058439 dated Oct. 8, 2020.

A. Ch. 6. Antibodies and cell receptors for them // Immunology / I. Roitt, J. Brostoff, D. Male—5th ed.—M.: Mir, 2000.—592 p.

Annex to the communication corresponding to European Patent Application No. 20716409.6 dated Jun. 27, 2024, 6 pages.

Holstein, M., et al., "Protein A Intermediate Wash Strategies", BioProcess International, Feb. 2015, 13(2), pp. 56-62.

International Preliminary Report on Patentability received in PCT Application No. PCT/EP2020/058439, mailed on Sep. 28, 2021, 6 pages.

Office Action (Decision to grant) corresponding to Japanese Patent Application No. 2021-558539 dated Aug. 1, 2023, pp. 6 (with Translation).

Office Action (Notice of Final Rejection) corresponding to Korean Application No. 10-2021-7034512 dated Aug. 9, 2024, 7 pages. (Translation).

Shukla, A.A., et al., "Host Cell Protein Clearance During Protein A Chromatography: Development of an Improved Column Wash Step," Biotechnology Progress, vol. 35, No. 5, pp. 1115-1121, Oct. 14, 2008.

Tomic, S., et al., "Complete clarification solution for processing high density cell culture harvests," Separation and Purification Technology, vol. 141, pp. 269-275, Feb. 12, 2015.

Office Action (First office action) corresponding to Korean Application No. 10-2021-7034512 dated Dec. 22, 2023, 8 pages. (Translation).

* cited by examiner

Figure 1: Process schemes of conventional purification methods for immunoglobulins
Figure 1A: Universal large-scale process
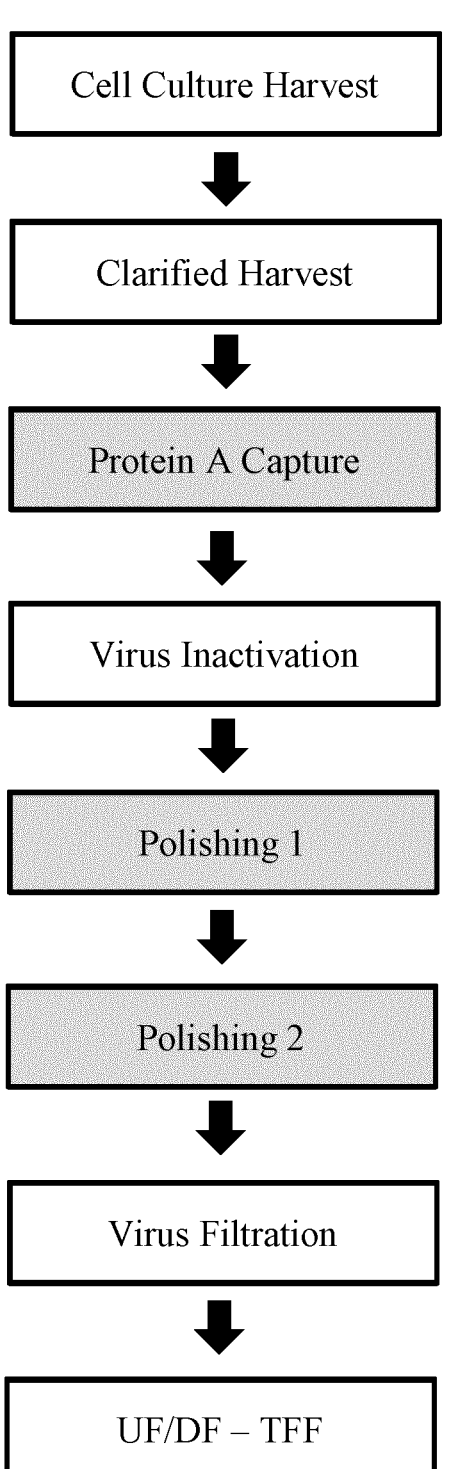

Figure 1: Process schemes of conventional purification methods for immunoglobulins
Figure 1B: Classical large-scale process
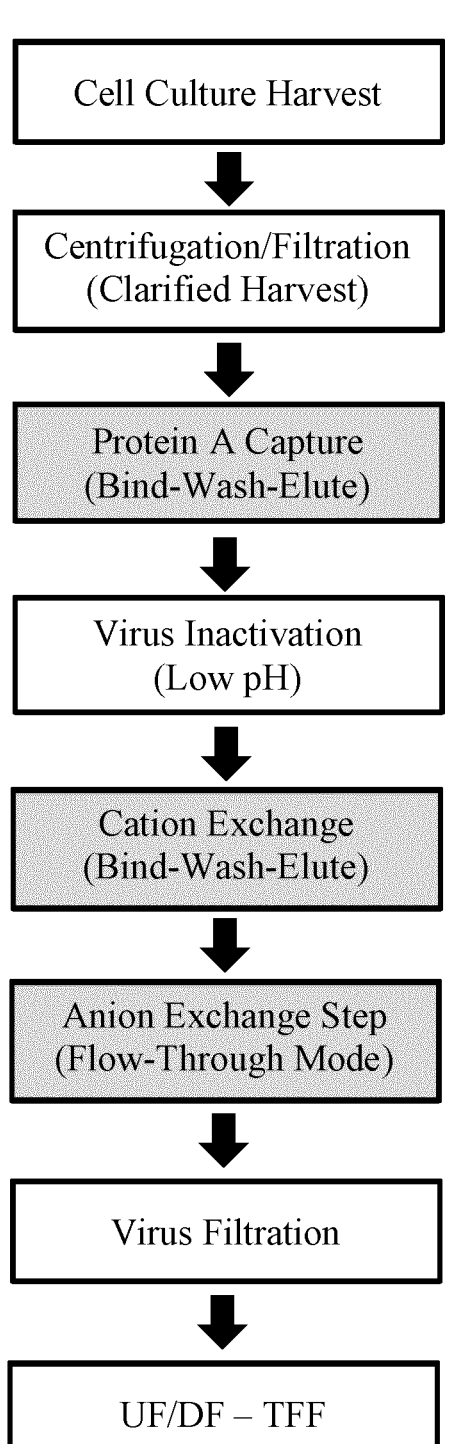

Figure 2:  Exemplary process schemes of the invention using pre-cleaning steps
Figure 2A: Large-scale process with pre-capture flocculation before cell separation
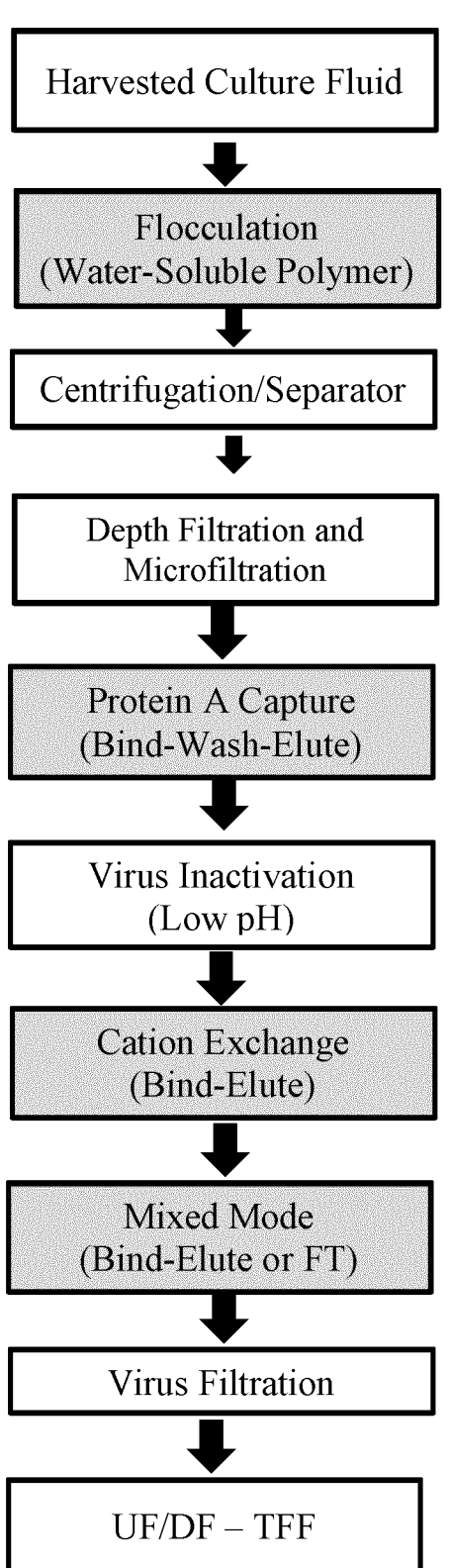

Figure 2: Exemplary process schemes of the invention using pre-cleaning steps
Figure 2B: Large-scale process with pre-capture flocculation after cell separation
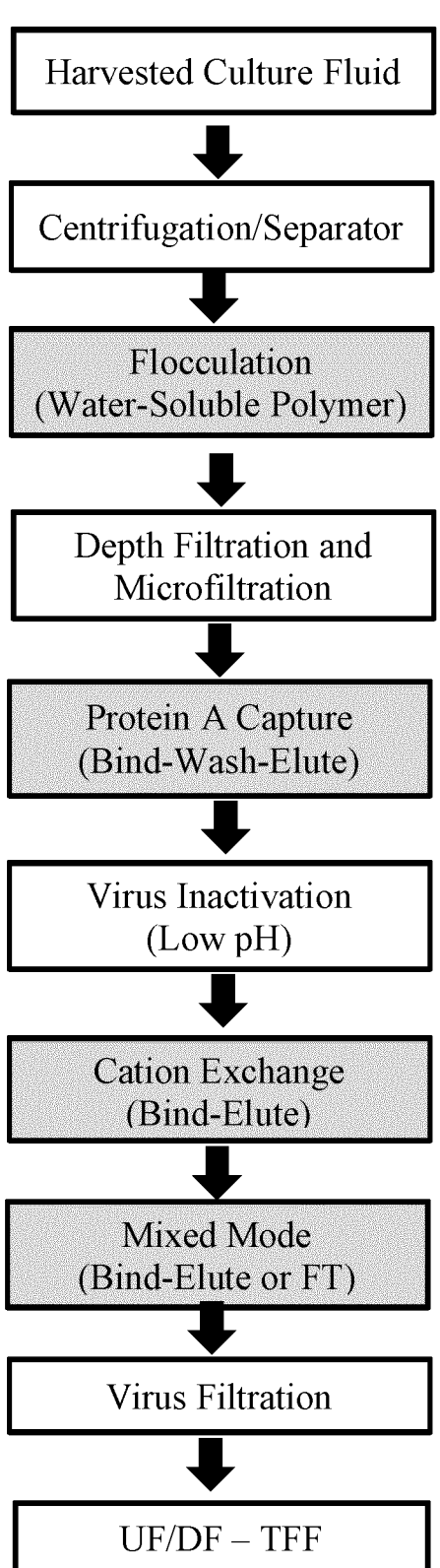

Figure 2: Exemplary process schemes of the invention using pre-cleaning steps
Figure 2C: Large-scale process with pre-capture flocculation after cell separation
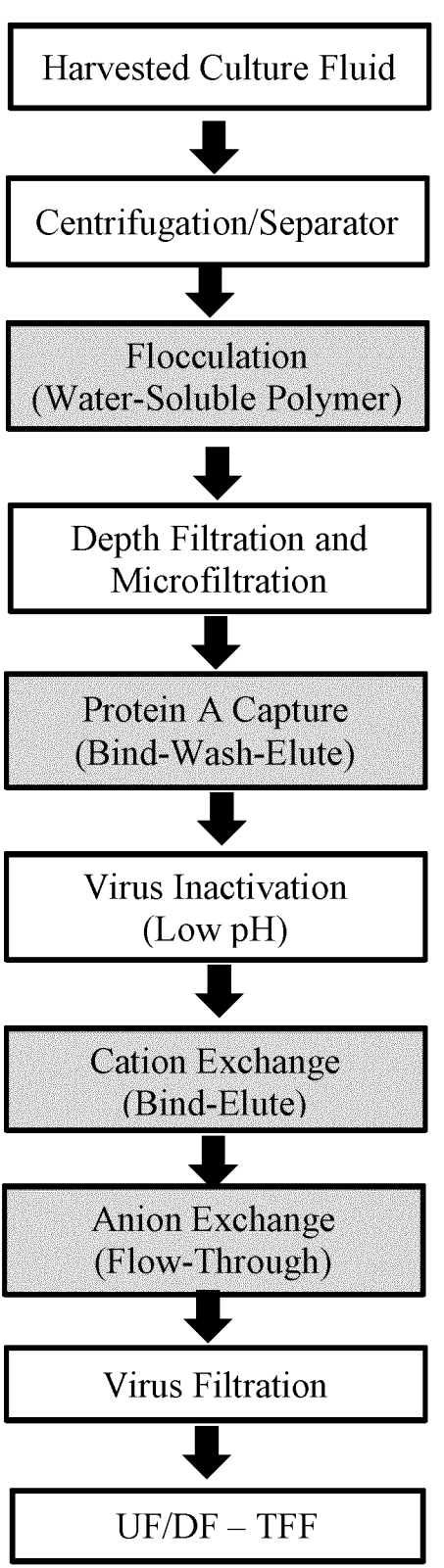

AFFINITY CHROMATOGRAPHY OF IMMUNOGLOBULINS BY USING PRE-CAPTURE FLOCCULATION

FIELD OF THE INVENTION

The present invention relates to methods for preventing precipitations during affinity chromatography of antibodies from a cell culture-derived composition using flocculation and filtration steps prior to the affinity capture chromatography and further polishing steps subsequent to the capture step to purify the antibodies.

BACKGROUND OF THE INVENTION

The selection of efficient and economic downstream sequences for purification of polypeptides produced by recombinant DNA technology is a crucial step in the development of every new biopharmaceutical intended for therapeutic use. In the recent past the need for large scale purification processes for monoclonal antibodies (mabs), due to their exceptionally high therapeutic dosages in medical use, has been further intensified with the use of improved cell culture methods resulting in higher cell densities, higher expression rates, and hence higher titer such as >10 g/L of the recombinant antibody of interest. The increasing concentrations in the culture fluids of product and contaminants set higher demands on the capture chromatography, on its preceding sample clarification steps, and on the subsequent polishing chromatographies. The entire downstream process has to: (i) manage an increased mass of product, (ii) efficiently remove increased process- and product-related impurities to below defined acceptance criteria, (iii) maintain economic yields, and (iv) assure sufficient quality of the mab. Usually, the downstream process accounts for a major part of the total manufacturing costs of therapeutic antibodies.

The mabs in crude fractions are typically associated with impurities such as host cell proteins (HCP), host cell DNA (HCDNA), endotoxins, insulin, viruses, aggregates, other undesired product variants, and various leachates from process materials. The presence of these impurities is a potential health risk for patients, and hence their absence from the final product is a regulatory requirement. Only very low residual amounts will be tolerated.

The classical procedure for purifying cell-culture derived polypeptides follows the sequence of capture-intermediate-polishing chromatographies, accompanied by filtration, concentration or dialysis steps at various positions of the downstream sequence. In recent years, platform approaches have been successfully established in the field of mab purification. Since mabs are a well-defined class of glycoproteins possessing common physicochemical properties, the use of a generic platform process is reasonable (Kelly B 2009). Such a universal process, with more or less product-specific adaptions, can be applied to many mabs, especially for those immunoglobulins of the same class or subclass, e.g. IgG1 or IgG2.

One of the most frequent capture step used for mab purification is affinity chromatography with Protein A. This capture offers exceptional selectivity for Fc-bearing molecules, thereby removing more than 99.5% of contaminants in a single step. However, besides its advantages, two disadvantages should also be mentioned. One draw back is the undesired leaching of Protein A or fragments of Protein A, which are known to be toxic (Gagnon P 1996). The other disadvantage is the high cost of this type of resin, particularly at the industrial scale necessary to purify sufficient amounts of therapeutic antibodies. A Protein A resin is approximately 30 times more expensive than an ion exchange resin. It was calculated that for the downstream processing of a 10 m³ cell culture the cost for the Protein A affinity chromatography is about 4-5 million USD (Farid S S 2009).

In many cases, capture steps are performed with crude input (load) materials, which can cause the contamination of (accumulation of impurities on) the affinity column resin. In absence of a proper regeneration step, this can prevent successful re-use of the capture resin. The contaminants in crude culture fluids, like lipids, oxidants, host cell proteins (HCP), host cell DNA (HCDNA), aggregates or particles, metal ions, and other substances promote fouling of the resins and can cause precipitations and turbidity during low pH elution (Shukla A A 2005). Besides direct effects on the binding moieties, also the matrix can be irreversibly contaminated. Increasing back pressure and reduced capacities and flow rates from run to run are the consequence. This problem is not limited to Protein A resins: fouling of chromatographic resins over their operational lifetimes is a general significant problem for commercial bioseparations. Hydrophobic ligands used for hydrophobic interaction chromatography and mixed-mode chromatography, when used as capture steps for cell culture-derived immunoglobulins, are especially susceptible for trapping lipophilic contaminants from the culture fluids. Despite sophisticated protocols for post-run cleaning steps, the lifetime of a capture column is limited and depends on the number of cycles, the operating conditions for running and cleaning, and the composition and purity of the sample.

To clarify and pre-clean the heavily contaminated culture fluids, mechanical separation steps have been employed which remove most of cell debris and aggregates. Centrifugation and filtration trains are the most common pre-treatment steps performed prior to loading the sample onto the capture resin. For large volumes, continuous centrifugation is performed by using cell separators followed by filtration steps using depth filters and/or micro filters. The resulting culture fluid is then referred to as "clarified cell culture supernatant" (Liu H F 2010). Although the direct load of harvested culture fluid onto the Protein A resin is a frequent method of choice (Fahrner R L 2001), other platform technologies make use of the various clarification steps, i.e. centrifugation, depth filtration, and/or microfiltration (Liu H F 2010, WO9522389, WO2001150110) in order to protect the capture column. This reduces the contamination of the resin with solids and particles and improves the purity of the antibody in the capture eluate. Pre-capture chromatography performed in flow-through mode, in addition to the centrifugation/filtration steps, was successfully demonstrated for large-scale purification of immunoglobulins (WO2015135884). It has been found, that by incorporating an additional anion exchange chromatography step upstream of the capture chromatography, the overall expense of the purification process can be significantly reduced. A pre-capture anion exchange flow-through chromatography step reduced the impurity burden to which the cost-intensive capture chromatography material is exposed.

Turbid elution pools and high column back pressure are common during elution of mabs by acidic pH in Protein A chromatography. Investigations linked this phenomenon to liquid-liquid phase separation as a result of protein self-association. Multiple factors, including pH, temperature, ionic strength, and protein concentration influence this effect. Careful selection of process parameters during Protein A elution, including temperature, flow rate, buffer, and salt can reduce both turbidity and column back pressure (Luo H 2017). Similar strategies have been taken to avoid the problems of aggregation and particulate formation, which manifested in turbidity of the Protein A elution pool (Shukla A A 2005). Stabilizing substances such as salts, urea, and amino acids added to the elution buffer, lower temperature, adaption of the pH values of wash and elution buffers, or pretreating the cell culture harvest to remove certain impurities that can precipitate at low pH were suggested. Among the pretreatment methods were anion exchange chromatography, filtration, and acid precipitation of contaminants (Shukla A A 2005).

Flocculation is a process that has been widely implemented in the chemical and food industries, as well as in wastewater treatment. Precipitation and flocculation are both successfully used for clarification of cell culture fluids. Whereas precipitation relies on lowering the solubility of target solutes in order to create solid particles, flocculation is the agglomeration of particles (cells, cell debris or colloids in mammalian cell culture) caused by a bridging effect induced by a flocculating agent. The flocculant triggers the destabilization of a biocolloidal suspension by causing the adhesion of dispersed particulates into larger-size clusters, resulting in an increase in the average particle size distribution. (Felo M 2015, Singh N 2016). Flocculation methods can be classified in anionic, cationic and mixed-mode flocculation (Singh N 2016).

Specifically, flocculants such as simple acids, divalent cations, polycationic polymers, caprylic acid and stimulus-responsive polymers have been evaluated for their ability to enhance cell culture clarification and reduce the levels of DNA, host cell proteins (HCP) and viruses (Felo M 2015). Since about ten years, flocculation methods have been intensively investigated for their usefulness in large-scale manufacturing of monoclonal antibodies, too.

Flocculation with combinations of various cations and anions, in presence of cells, with and without pH adjustments, was successfully applied for purification of monoclonal antibodies (WO2007035283). Most preferred was the combination of $Ca^{2+}$ and phosphate. A prominent reduction of HCP and turbidity in the Protein A elution peak compared to non-flocculated controls was emphasized.

Other methods make use of polyelectrolytes, such as polyvinylsulfonic acid, polyvinylsulfonate, polystyrenesulfonic acid, polyacrylic acid, polylysine, or polyarginine for precipitation of impurities in harvested cell culture fluids (WO2008091740). A similar method using caprylic acid as flocculant was developed to precipitate contaminants (WO2010151632). The precipitation or flocculation of impurities often requires additional pH manipulation. This was disclosed for the precipitation with divalent cations, such as $Co^{2+}$ or $Ni^{2+}$ (WO2008127305) and the precipitation with dextran (WO2016153983).

Another flocculation process using benzylated poly (allylamine) referred to as stimulus-responsive polymer, was developed for monoclonal IgG1 purification from CHO cell culture.

The stimulus was set by adding sodium phosphate (Kang Y K 2013). Further compounds acting as stimulus-responsive polymers in clarification of cell culture harvest of antibodies are known (WO2011146394).

A flocculation step by adding allantoin to cell-containing harvest, followed by the addition of ethacridine, was described as a conditioning method prior to subsequent adsorption and chromatographic steps (WO2014133459).

Another flocculation method makes use of a $C_7$-$C_{10}$ fatty acid in combination with further functional substrates for clarification of cell culture harvest (WO2014196926). A similar process based on a combination of $C_7$-$C_{10}$ fatty acid and allantoin was applied (WO2015130222).

A more complex flocculation method was disclosed by the combination of allantoin, cationic polymer, and a fatty acid for removing of contaminants in cell-containing harvest. The mixture of three flocculants, allantoin, chitosan, and caprylic acid, was most successful (WO2017217930).

An entire process for purification of antibodies or other target molecules and comprising (i) a precipitation step for removal of contaminants, (ii) a Protein A chromatography followed by (iii) one or two flow through chromatographies was described (WO2014004281). The precipitant is added to the cell culture harvest and comprises flocculants, too, with and without additional stimulus-responsive elements.

The application of poly (diallyldimethylammonium chloride), a cationic water-soluble polymer, was investigated for the clarification of harvest of mab-producing CHO cell culture (McNerney T 2015). The authors added the flocculant directly to the culture broth. Centrifugation was omitted in favor of a filtration train. It was shown that the toxic poly (diallyldimethylammonium chloride) was reduced to non-detectable levels after a subsequent Protein A capture chromatography.

A large-scale cell culture harvest method consisting of an initial flocculation step in presence of cells and based on poly (diallylmethylammonium chloride) was developed (WO2013090820). The preferred flocculation method makes use of further enhancers of flocculation, i.e. polyethylene glycol and Triton X-100.

SUMMARY OF THE INVENTION

The present invention relates to the prevention of precipitations during low pH elution of immunoglobulins from cell cultures from affinity capture chromatographic media. The invention further provides methods for purifying an immunoglobulin in an efficient and cost-effective manner and with satisfactory purity and yield. In particular, the present invention aims improving the purity of the immunoglobulin solution eluted from the capture chromatography resin and hence results in an improved quality of the final product.

Furthermore, the present invention addresses the aspect of the re-use of the rather cost-intensive chromatography materials, in particular the lifetime of the affinity chromatography materials used in the capture step of the downstream process, and how this can be increased, while reducing the technical complexity of the purification process.

Conventional downstream chromatography processes for the purification of immunoglobulins from cell culture fluids usually start with an affinity capture chromatography step in which the immunoglobulin has to be captured from a sample comprising the immunoglobulin together with impurities. The immunoglobulin is separated from the impurities largely because of the selective binding of the immunoglobulin to the affinity ligands of the capture chromatography resin while the impurities do not bind to the resin and are thus obtained in the flow-through, whereas the immunoglobulin is obtained in the eluate.

The affinity capture chromatography is usually the most expensive step in the purification of immunoglobulins, amounting to 40 to 50% of the overall downstream process costs in the case when a Protein A affinity chromatography is used. The same applies to alternative affinity chromatography columns, which may be used as a capture chromatography step in the purification of immunoglobulins.

There is an ongoing need for cost-effective purification of immunoglobulins from large volumes of cell culture fluid and fermentation broth and from clarified samples derived from such fluid or broth. In particular, there is a need for simple purification methods that are cost-effective and still efficient and satisfactory in terms of purity and yield.

It has been found that by incorporating an additional chromatography step upstream of the capture chromatography, the overall expense of the purification process can be significantly reduced. This additional chromatography step reduces the impurity burden to which the cost-intensive capture chromatography material is exposed. This so called "pre-cleaning" step is carried out using anion exchange or mixed-mode chromatography material that is less expensive and more robust compared to the chromatography material used in the subsequent capture step and is easy to regenerate (WO2015135884). In order to keep the purification process as simple as possible, the pre-cleaning chromatography is performed in the flow-through mode, i.e. the immunoglobulin to be purified is not bound by the resin and thus obtained in the flow-through fraction, while impurities are largely retained on the resin and thereby separated from the immunoglobulin. A direct connection of the pre-cleaning anion exchange column with the Protein A capture column, so that the flow-through of the pre-cleaning step is not temporarily stored in a collecting vessel, but is immediately passed to the capture chromatography resin, further simplifies this method (WO2015135884).

Nevertheless, such a process of anion exchange flow through chromatography used as a pre-capture clarification step, although successfully established in large-scale production, is still subject for further improvements. An anion exchange chromatography depletes mainly negatively charged substances, such as HCDNA and HCP, together with non-specifically adsorbed cell debris, aggregates, lipids, etc. which are retained by the column. However, the majority of positively charged HCP and uncharged molecules can pass the pre-cleaning column. This can lead to an undesired turbidity in the Protein A elution peak. Moreover, due to the increasing demands caused by the high cell densities, complex media feeding strategies, and high expression rates of state-of-the-art mammalian cell cultures, the pre-cleaning column is required with a significant dimension to act as an efficient protective shield of the Protein A column. This comes at a price. Finally, the anion exchange resin has to undergo harsh and time-consuming cleaning and regeneration procedures. This is disliked in routine production, which is preferentially performed in campaigns of serial batches.

The present invention studied the feasibility of a flocculation step used as a pre-capture step to overcome the aforementioned problems of a chromatographic pre-cleaning. In order to achieve the required high purity of the immunoglobulin intended for therapeutic use, two or more chromatographic polishing steps are following the flocculation step and the capture chromatography step.

The problem underlying the present invention is solved by the provision of a method for purifying an immunoglobulin from a cell culture fluid, the method comprising the following steps in the following order:
    (a) adding a flocculation-inducing compound to the cell culture fluid;

(b) depth filtration of the mixture of step (a);
    (c) exposing the filtrate obtained in step (b) to affinity chromatography, wherein the immunoglobulin is bound to the affinity chromatography medium;
    (d) washing the affinity chromatography medium using a washing buffer with a pH value of 5 to 9 and a ionic strength of 0.1 to 5.0 mol/l; and
    (e) eluting the immunoglobulin from the affinity chromatography resin using an elution buffer with a pH value of 2.5 to 4.5.

In some embodiments, step (a) comprises the following steps
    centrifugation and/or filtration of the cell culture fluid;
    adding a flocculation-inducing compound to the supernatant or filtrate.

The flocculation may be performed by adding a cationic compound as flocculant. The cationic compound may be selected from the group consisting of a divalent metal ion salt, a water-soluble organic polymer, and a water-insoluble organic polymer.

In some embodiments, the divalent metal ion salt is $CaCl_2$).

In some embodiments, the water-soluble organic polymer is poly (diallyldimethylammonium chloride). In other embodiments, the water-insoluble organic polymer is chitosan.

In specific embodiments, the flocculation is performed with poly (diallyldimethylammonium chloride) as flocculant. More specifically, the poly (diallyldimethylammonium chloride) has a molecular mass of 10 kDa to 10 000 kDa.

Typically, the poly (diallyldimethylammonium chloride) is added in a final concentration of 0.01 to 1.0% (w/v), preferably in a final concentration of 0.02 to 0.1% (w/v), more preferably in a final concentration of 0.03 to 0.08% (w/v).

In some embodiments, no further substances except the poly (diallyldimethylammonium chloride) are added for performing the flocculation.

In some embodiments, the flocculation with poly (diallyldimethylammonium chloride) is performed without further adjustment of pH or conductivity.

In specific embodiments, the flocculation is performed under stirring, at room temperature, for at least 5 min, preferably for at least 15 min.

In preferred embodiments, the affinity chromatography is a Protein A chromatography. The Protein A chromatography medium may comprise an alkali-tolerant Protein A derivative as a ligand, preferably an alkali-stabilized tetramer variant of domain B of Protein A, bound to a cross-linked agarose matrix.

In some embodiments, after depth filtration microfiltration is carried out.

Typically affinity chromatography is carried out at most 8 h after depth filtration, preferably at most 3 h after depth filtration.

In some embodiments, the cell culture fluid is obtained from recombinant CHO cells expressing the immunoglobulin. Preferably, the immunoglobulin is IgG1 or IgG2. More preferably, the Fc part of the IgG1 or IgG2 is human.

The method as described herein may comprise the steps as defined in any one of the previous embodiments and comprising one or more further steps following the affinity chromatography selected from virus inactivation, ion exchange chromatography, mixed-mode chromatography, nanofiltration, and ultrafiltration/diafiltration.

Preferably the method described above further comprises the following steps:

(f) incubating the eluate of step (e) for virus inactivation at a low pH value of 2.5 to 4.5, for at least 10 minutes;

(g) performing a cation exchange chromatography;

(h) performing a mixed-mode chromatography or an anion exchange chromatography;

(i) exposing the eluate of step (h), or a composition derived therefrom and obtained after one or more further processing steps performed after step (h) to nanofiltration; and (j) exposing the filtrate of step (i), or a composition derived therefrom and obtained after one or more further processing steps performed after step (i) to ultrafiltration/diafiltration.

A further preferred method comprises the following steps in the following order:

(a) adding a flocculation-inducing compound to the cell culture fluid;

(b) depth filtration of the mixture of step (a);

(c) exposing the filtrate obtained in step (b) to affinity chromatography, wherein the immunoglobulin is bound to the affinity chromatography medium;

(d) washing the affinity chromatography medium using a washing buffer with a pH value of 5 to 9 and a ionic strength of 0.1 to 5.0 mol/l; and (e) eluting the immunoglobulin from the affinity chromatography resin using an elution buffer with a pH value of 2.5 to 4.5.

(f) incubating the eluate of step (e) for virus inactivation at a low pH value of 2.5 to 4.5, for at least 10 minutes;

(g) performing a cation exchange chromatography;

(h) performing a mixed-mode chromatography or an anion exchange chromatography;

(i) exposing the eluate of step (h), or a composition derived therefrom and obtained after one or more further processing steps performed after step (h) to nanofiltration; and (j) exposing the filtrate of step (i), or a composition derived therefrom and obtained after one or more further processing steps performed after step (i) to ultrafiltration/diafiltration;

Wherein step g) is performed in bind-elute mode and step h) in bind-elute mode or in flow-through mode.

The invention further solves the problem of increasing viral safety in a manufacturing process of an immunoglobulin.

BRIEF DESCRIPTION OF THE DRAWINGS

FIG. 1: Process schemes of conventional purification methods for immunoglobulins FIG. 1A shows a universal process scheme for purification of immunoglobulins from large volumes of cell cultures. The process, which started from the clarified bulk material, which is obtained after centrifugation and/or filtration of the harvested culture fluid, consists of a Protein A capture step and two subsequent polishing steps. This scheme includes two typical virus safety steps, too. A virus inactivation step is performed by keeping the Protein A eluate at low pH and a nanofiltration step for virus removal is performed after the last polishing step. The final step is usually a tangential flow ultrafiltration and/or diafiltration (UF/DF-TFF) to set the desired concentrations of the immunoglobulin and those of the formulation ingredients.

FIG. 1B shows a classical process scheme for purification of immunoglobulins from large volumes of cell cultures consisting of three chromatographies (e.g. according Fahrner R. L. 2001 or Kelly B. 2009). It is the same process as in FIG. 1A except that the polishing steps are disclosed to be a cation exchange chromatography (polishing step 1) followed by an anion exchange chromatography (polishing step 2). It has to be emphasized that the cation exchange chromatography is performed in a binding mode, whereas the anion exchange chromatography is performed in a flow-through mode. It should be mentioned, that a frequently applied equivalent variant of this classical scheme is simply to change the order of polishing step 1 and 2.

FIG. 2: Exemplary process schemes of the invention using pre-cleaning steps

FIG. 2A shows a large-scale process scheme with a pre-capture flocculation step directly in the harvest in the presence of cells. The flocculated material is then removed by centrifugation followed by depth filtration and microfiltration. The flocculation step is performed by adding a cationic compound. The clarified culture fluid is loaded on the capture chromatography column, which is Protein A. The two polishing steps are a cation exchange chromatography (polishing step 1) followed by a mixed-mode chromatography (polishing step 2). The cation exchange chromatography is performed in the bind and elute mode. The mixed-mode resin has positively charged ligands and can be performed in bind and elute mode or in flow-through (FT) mode. The intermediate viral safety steps and the final UF/DF-TFF are as described under FIG. 1A.

FIG. 2B shows an alternative large-scale process scheme, which is similar to the process of FIG. 2A except that the flocculation step is performed after the cell separation in absence of cells. All the other steps are as described under FIG. 2A.

FIG. 2C shows another alternative large-scale process scheme, which is similar to the process of FIG. 2B except that the final polishing chromatography is anion exchange chromatography in flow-through (FT) mode. All the other steps are as described under FIG. 2B and FIG. 2A.

DETAILED DESCRIPTION OF THE INVENTION

As used herein, the term "cell culture fluid", refers to a harvested cell culture fluid, cell culture supernatant or pretreated cell culture supernatant. The cell culture fluid can be obtained directly from a host cell or organism producing the immunoglobulin. The cell culture fluid may have been partially clarified or purified by centrifugation and/or filtration, for example microfiltration, diafiltration, ultrafiltration and depth filtration.

As used herein, the term "pretreated" refers for example to a cell culture supernatant that has been prepared for a chromatography step used in a method of the invention, for example by subjecting the sample to one or more adjustments consisting of buffer exchange, dilution, addition of salts, detergents, chaotropic substances, or organic compounds, pH titration or filtration in order to adjust the pH and/or conductivity range and/or buffering capacity to achieve a desired chromatography performance and to stabilize the immunoglobulin. As immunoglobulins expressed from mammalian cells are usually secreted into the cell culture fluid during the cultivation process, the product harvest at the end of the cultivation process occurs by separating cell culture fluid from the cells. The cell separation method should be gentle to minimize cell disruption to avoid the increase of cell debris and release of proteases and other molecules that could affect the quality of the immunoglobulin product. Usually, the harvest from mammalian cell cultures undergoes centrifugation followed by filtration. Expanded bed adsorption chromatography is an alternative method to avoid centrifugation/filtration methods. Other treatments of the sample prior to the purification via chromatographic steps may be concentrating and/or diafiltrating of the cell culture supernatant into specific immunoglobulin concentration, range of pH, conductivity, and buffer species concentration.

As used herein the term "flocculation" (synonyms "coagulation" and "agglomeration") comprises a clustering reaction whereby suspended solids in a fluid interact with the flocculation-inducing agent resulting in the formation of larger-size aggregates or flocs. The terms "flocculants" and "flocculation-inducing agents" which can be used interchangeably herein, may be cationic or anionic compounds. Preferably, the flocculants are cationic compounds. More preferably, the flocculants are cationic water-soluble polymers. A "flocculation step" as applied in the present invention functions as a pre-cleaning step upstream to the capture chromatography. The flocculation can be performed either in presence of cells, this means the flocculant is directly added to the cell culture fluid at the end of cultivation, and the flocculated material including the cells is removed from the cell culture fluid by centrifugation and/or filtration, or the flocculant is added to the cell culture fluid after the cells have been removed by centrifugation, and the flocculated material is then removed by filtration.

As used herein the term "cationic compound" comprises metal ions and cationic polymers (polycations). "Cationic polymers" can be water-soluble polymers or water-insoluble polymers. "Water-soluble polymers" comprise organic substances that dissolve in water and thus modify the physical properties of aqueous systems. "Water-insoluble polymers" have limited solubility in water. They disperse or swell in water and comprise preferably hydrophilic polymers, which functions as flocculant in aqueous suspension. Water-insoluble polymers may become soluble in water at very low or very high pH. The cationic compounds used as flocculant perform a variety of functions in aqueous media. Water-soluble or water-insoluble organic polymers comprise a wide range of substances derived from natural sources or from chemical synthesis. Examples for natural water-soluble or water-insoluble organic polymers are polysaccharides (e.g. pectin, dextran, starch, chitosan, and hyaluronic acid), xanthan gum, carrageenan, among many others. Examples for chemically synthesized organic polymers are polyethylene glycol (PEG), polyvinyl pyrrolidone (PVP), polyvinyl alcohol (PVA), polyacrylic acid (PPA), polyacrylamide, among many others (for review see Kadajii V G 2011). In the course of this invention the water-soluble polymers function as the most preferred flocculants.

The terms "impurity" and "contaminant" are used interchangeably herein and refer to any material that is different to the immunoglobulin of interest. Examples may be cell culture media components, cell debris, host cell proteins, endotoxins, viruses, lipids, DNA, RNA, leachates from process materials, and aggregates or fragments thereof. Also considered as impurities are product-related substances such as aggregates, charge variants, misfolded molecules, or fragments of the immunoglobulin of interest to be purified.

The term "precipitation" refers to impurities, which are non-soluble and/or are in a non-soluble state. Precipitations may lead to turbidities of the sample.

As used herein the term "chromatography media" or "chromatography medium" has to be understood as a chromatography material or media in form of beads, plates, crystals, monoliths, membranes, fibers, meshwork of fibers or any other solid phase. The "media" bears functional groups referred to as "ligands" bound to a backbone, directly or via spacer, referred to as "matrix". An exception are gel chromatography resins for size exclusion chromatography which are typically without any attached ligand. The term "media" does not limit the methods of the invention to only column chromatography employing chromatography resins but also includes other types of chromatography, for example membrane chromatography employing membrane adsorbers. In particular, in ion exchange chromatography an ion chromatography exchange resin or a ion exchange chromatography membrane adsorber are both comprised by the invention.

"Resin" means any chromatographic material or media in form of beads comprising a matrix with a bound functional group (ligand) which may interact with the protein or at least one contaminant. An exception are gel chromatography resins for size exclusion chromatography which are typically without any attached ligand. Resins may be supplied as beads of different sizes and packed in columns. Alternatively, pre-packed columns may be purchased.

By the terms "matrix" or "solid phase" is meant a non-aqueous matrix to which the ligand can adhere. The matrix of interest herein is generally one, which comprises glass, ceramic, silica, cellulose, agarose, methacrylate polymer or polystyrene.

By "ligand" is meant any functional group, which interacts with the protein or with at least one contaminant and which is covalently bound to the "matrix".

The term "binding mode" or "bind and elute mode" refers to chromatography conditions in which a sample containing the immunoglobulin to be purified is applied to a chromatography medium, wherein the immunoglobulin binds to the chromatography medium. Thus, the immunoglobulin is retained on the chromatography medium, whereas the impurities of the sample may be present in the non-binding fraction, also called the flow-through fraction. When a chromatography step is carried out in the binding mode, one or more washing steps may be performed after the binding of the immunoglobulin to the chromatography medium and prior to eluting the immunoglobulin from the medium. To obtain the immunoglobulin, the immunoglobulin is then eluted and obtained in the eluate, which may then further be purified in a further chromatographic step, if desired. Elution of the immunoglobulin may be performed using selective conditions permitting contaminants to remain bound to the medium while the immunoglobulin is eluted.

Performing a chromatography step in the "binding mode" does not necessarily mean that 100% of the immunoglobulin of interest is bound. In the context of the present invention, "bound to the chromatography resin" or "bound to the chromatography medium" means that at least 50% of the immunoglobulin is bound, preferably at least 75% of the immunoglobulin is bound, more preferably at least 85% of the immunoglobulin is bound, and most preferably more than 95% of the immunoglobulin is bound to the resin or medium.

In the context of the present invention, it is understood, that the capture chromatography step and the intermediate cation exchange chromatography step, are both performed in the binding mode, wherein the capture step is considered the first chromatography step, which is performed in the binding mode. The final polishing mixed-mode chromatography step of the invention is performed either in bind and elute mode or in flow-through mode. It is further understood, that instead of the mixed-mode chromatography an anion exchange chromatography in flow-through mode can be used as the final polishing step.

The term "flow-through mode" refers to chromatography conditions in which a sample containing the immunoglobulin of interest is applied to the chromatography resin or medium, wherein the immunoglobulin does not bind to the chromatography resin but is mainly present in the fraction that is not bound to the resin or medium and thus contained in the flow-through. The developed intermediate chromatographies of the present invention do not make use of the flow-through mode. However, the methods of the present inventions can be supplemented by additional polishing chromatographies in a flow though mode. Impurities may bind to the resin or medium in this mode.

The "wash step" is a step performed in a chromatography in binding mode, after the sample is loaded onto the chromatography column, but before the protein is eluted from the column. The wash step additionally removes contaminants less tightly or nonspecifically bound to the matrix, to the immunoglobulin, and/or to the ligand, without significantly eluting the immunoglobulin of interest from the resin. In the wash step, the resin is washed with the desired wash buffer (e.g. the wash buffer is passed through the chromatography column until the UV absorption measured in the outlet of the column returns to baseline).

The term "elution" is understood as a process, which desorbs an immunoglobulin of interest from a chromatography resin by altering the solution conditions such that buffer components compete with the molecule of interest for the ligand site on the chromatography resin. Another mode of elution occurs in affinity chromatography, for example using Protein A. In this case, the elution buffer may alter the conformation of the ligand or the immunoglobulin, thereby loosening the binding. An immunoglobulin of interest may be eluted from ion exchange resins by altering the ionic strength of the buffer surrounding the ion exchange material such that the buffer ions in the mobile phase compete with the molecule for the charged ionic sites of the ion exchange resin. Alternatively, a change in the pH influences the amphoteric protein and a pH increase above the pI of the protein henceforth prevent its binding to a cation exchange resin and the protein elutes. The same effect occurs on an anion exchange chromatography resin, when the pH is decreased below the pI of the protein. As understood herein the term "elution" comprises isocratic elution, single step elution, and gradient elution, with or without preceding wash steps. The elution of the immunoglobulin of interest may be conducted by increasing the ionic strength or conductivity in the mobile phase, which is affected by increasing the salt concentration in the buffer solution. Alternatively, an increase or decrease in the pH value may be suitable. Discontinuous step gradients, linear gradients, nonlinear gradients or a suitable combination of such gradients may be employed.

Buffers suitable for washing and for the elution can be selected from acetate, citrate, succinate, maleate, malonate, Tris-HCl, Tris-acetate, Tris-glycine, phosphate, succinate, malonate, MES, MOPS, PIPES, PHEPES, bistris, glycine, and other suitable buffers with the addition of salts such as phosphates, sulfates, or chlorides, such as NaCl or KCl. The ionic strength and the salt concentration, by means of which the elution is achieved, are dependent on the pH value of the buffer solution and the pI of the protein. The wash buffer may further comprise detergent (e.g. polysorbate), solvent (e.g. hexylene glycol, ispropanol, or ethanol), or polymer (e.g. polyethylene glycol). Furthermore, the wash buffer may include chaotropic reagents (e.g. urea or arginine) and/or protease inhibitors (e.g. EDTA).

As used herein the term "buffer" refers to a solution that resists changes in the pH by the action of acid-base conjugate components.

The terms "immunoglobulin" and "antibody" are used interchangeably herein. The immunoglobulin may be a monoclonal antibody, polyclonal antibody, multispecific antibody (e.g. bispecific antibody) and fragments thereof exhibiting the desired antigen binding activity. Naturally occurring antibodies are molecules with varying structures. For example, native IgG antibodies are hetero tetrameric glycoproteins of about 150,000 Daltons, composed of two identical light chains and two identical heavy chains that are linked by disulfide bonds. From N- to C-terminus, each heavy chain has a variable domain (VH), also called a variable heavy domain or a heavy chain variable domain followed by three or four constant domains (CH1, CH2, CH3 and optionally CH4). Similarly, from N- to C-terminus, each light chain has a variable domain (VL), also called a variable light domain or a light chain variable domain followed by a constant light chain (CL) domain. The light chain of an antibody may be assigned to one of two types, called kappa ($\kappa$) and lambda ($\lambda$), based on the amino acid sequence of its constant domain.

"Antibody fragments" comprise a portion of a full length antibody, generally the antigen binding or variable region thereof. Examples of antibody fragments include Fab, Fab', $F(ab')_2$, and Fv fragments; single-chain antibody molecules; diabodies; linear antibodies; and multispecific antibodies formed from antibody fragments.

Preferably the immunoglobulin is a monoclonal antibody. The term "monoclonal antibody" as used herein refers to an antibody obtained from a population of substantially homogeneous antibodies, i.e. the individual antibodies comprising the population are identical except for possible naturally occurring mutations that may be present in minor amounts. In contrast to conventional (polyclonal) antibody preparations, which typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method.

The immunoglobulin may be of the murine class IgG1, IgG2a, IgG2b, IgM, IgA, IgD or IgE, the human classes IgG1, IgG2, IgG3, IgG4, IgM, IgA1, IgA2, IgD or IgE, or combinations or fragments thereof.

The immunoglobulin may recognize any one or a combination of proteins including, but not limited to the following antigens: CD2, CD3, CD4, CD8, CD11a, CD14, CD18, CD19, CD20, CD22, CD23, CD25, CD33, CD40, CD44, CD52, CD80) (B7.1), CD79b, CD86 (B7.2), CD147, CD152, IL-1a, IL-1ß, IL-1, IL-2, IL-3, IL-7, IL-4, IL-5, IL-8, IL-10, IL-12, IL-13, IL-23, IL23a, IL-2 receptor, IL-4 receptor, IL-6 receptor, IL-12 receptor, IL-13 receptor, IL-18 receptor subunits, PDGF-$\beta$, and analogues thereof, PLGF, VEGF, TGF, TGF-$\beta$2, TGF-p1, EGF receptor. PLGF receptor, VEGF receptor, platelet receptor gpIIb/IIIa, thrombopoeitin receptor, apoptosis receptor PD-1, hepatocyte growth factor, osteoprotegerin ligand, interferon alpha, interferon beta, interferon gamma, B lymphocyte stimulator BLyS, T-cell activation regulator CTLA-4, C5 complement, IgE, tumour antigen CA125, tumour antigen MUC1, PEM antigen, ErbB2/HER-2, tumour-associated epitopes that are present in elevated levels in the sera of patients, cancer-associated epitopes or proteins expressed on breast, colon, squamous cell, prostate, pancreatic, lung, and/or kidney cancer cells and/or on melanoma, glioma, or neuroblastoma cells, the necrotic core of a tumour, integrin alpha 4 beta 7, the integrin VLA-4, B2 integrins, $\alpha4\beta1$ and $\alpha4\beta7$ integrin, TRAIL receptors 1, 2, 3, and 4, RANK, a RANK ligand (RANKL), TNF-$\alpha$, the adhesion molecule VAP-1, epithelial cell adhesion molecule (EpCAM), intercellular adhesion molecule-3 (ICAM-3), leukointegrin adhesin, the platelet glycoprotein gp IIb/IIIa, cardiac myosin heavy chain, parathyroid hormone, sclerostin, MHC I, carcinoembryonic antigen (CEA), calcitonin gene-related peptide (CGRP), alpha-fetoprotein (AFP), tumour necrosis factor (TNF), Fc-y-1 receptor, HLA-DR 10 beta, HLA-DR antigen, L-selectin, Kallikrein, Kirin, and IFN-$\gamma$.

The immunoglobulin may be for example afelimomab, abciximab, adalimumab, ado-trastuzumab, aducanumab, alemtuzumab, alirocumab, anifrolumab, arcitumomab, atezolizumab, avelumab, basiliximab, belimumab, benralizumab, bevacizumab, bezlotoxumab, blinatumomab, bocozizumab, brazikumab, brentuximab, brodalumab, brolucizumab, canakinumab, caplacizumab, capromab, cemiplimab, certolizumab, cetuximab, clenoliximab, claudiximab, crizalizumab, daclizumab, daratumumab, denosumab, dinutuximab, dupilumab, durvalumab, eculizumab, edrecolomab, elotuzumab, emicizumab, eptinezumab, erenumab, evinacumab, evolocumab, fremanezumab, foravirumab, galcanezumab, galiximab, gemtuzumab, golimumab, guselkumab, ibalizumab, ibritumomab, imciromab, idarucizumab, inebilizumab, infliximab, inotuzumab, ipilimumab, ixekizumab, keliximab, lanadelumab, lebrikizumab, lexatumumab, mavrilimumab, mepolizumab, mirikizumab, mogamulizumab, mosunetuzumab, muromonab-CD3, natalizumab, necitumumab, nivolumab, nofetumomab, obinutuzumab, ocrelizumab, ofatumumab, olaratumab, omalizumab, palivizumab, panitumumab, pembrolizumab, pertuzumab, polatuzumab, ramucirumab, ranibizumab, ravulizumab, restizumab, risankizumab, rituximab, rovalpituzumab, sacituzumab, sarilumab, satralizumab, secukinumab, sirukumab, tanecumab, tezepelumab, tezolizumab, tocilizumab, tositumomab, tralokinumab, trastuzumab, tremelimumab, ublituximab, ustekinumab, and vedolizumab.

The immunoglobulin of the invention is preferably an IgG molecule, such as IgG1, IgG2, IgG3, or IgG4 molecule. More preferably, the immunoglobulin is IgG1 or IgG2. Even more preferably, the immunoglobulin is an IgG1 or IgG2 wherein at least the Fc part is human. The immunoglobulin may be a murine-human chimeric IgG1 wherein the Fc part of the IgG1 is human. Most preferably, the chimeric immunoglobulin is rituximab or infliximab.

Rituximab is a chimeric anti-CD20 antibody, which is described in detail in, for example, WO9411026.

Infliximab is a chimeric anti-TNF$\alpha$ antibody, which is described in detail in, for example, WO9216553.

The immunoglobulin may be a humanized IgG1 form a murine progenitor. Most preferably, the humanized antibody is trastuzumab or bevacizumab.

Trastuzumab is a humanized anti-HER2 antibody, which is described in detail in, for example, WO9222653.

Bevacizumab is a humanized anti-VEGF antibody, which is described in detail in, for example, WO9845331.

The immunoglobulin may be a fully human IgG1 or IgG2 antibody. Most preferably, the human antibody is adalimumab (IgG1) or denosumab (IgG2).

Adalimumab is a human anti-TNF$\alpha$ antibody, which is described in detail in, for example, WO9729131.

Denosumab is a human anti-RANKL antibody, which is described in detail in, for example, WO03002713.

In one embodiment the immunoglobulin is bevacizumab, trastuzumab, or denosumab.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity.

Furthermore, the monoclonal antibodies herein also include "humanized" antibodies. Such antibodies are obtained by "humanization" of non-human (for example murine) antibodies and contain only minimal sequences derived from the animal immunoglobulin. Most of the molecule is human sequence. Residues from a hypervariable region of the human recipient antibody are replaced by residues from a hypervariable region of a non-human donor antibody having the desired binding properties.

Finally, the monoclonal antibodies herein also include fully human antibodies, which may be obtained by screening of a human antibody gene library.

In a preferred embodiment, the sample is derived from a cell culture fluid, which is obtained from recombinant CHO cell culture. Preferably, the cell culture fluid is obtained from a recombinant cell culture in the growing phase.

The method of the invention may be used for immunoglobulin purification on a small and large scale. Preferably, the method is carried out on a large scale.

"Small scale", also denoted as "laboratory scale", refers to purification of samples containing less than 50 g immunoglobulin, less than 10 g immunoglobulin, or less than 1 g immunoglobulin. "Small scale" also refers to purification processes in which the protein eluted from the column of the capture step amounts to less than 50 g immunoglobulin, less than 10 g immunoglobulin, or less than 1 g immunoglobulin.

"Large scale", also called as "production scale" or "manufacturing scale" or "commercial scale", refers to purification of samples containing more than 50 g immunoglobulin, more than 100 g immunoglobulin, more than 200 g immunoglobulin or more than 300 g immunoglobulin. "Large scale" also refers to purification processes in which the protein eluted from the column of the capture step amounts to more than 50 g immunoglobulin, more than 100 g immunoglobulin, more than 200 g immunoglobulin or more than 300 g immunoglobulin.

The term "further processing step" refers to any step that is commonly applied within protein purification protocols such as filtration, dialysis, virus inactivation, dilution, concentration, adjustments in pH, adjustments of conductivity, an intermediate chromatography step or a hold step for any purpose. A further processing step can be applied between all chromatography steps of the invention. An intermediate chromatography step can be applied between any of the chromatography steps. In particular, the term "further processing step" refers to an intermediate chromatography step applied between the capture chromatography and the cation exchange chromatography. The intermediate chromatography step may be carried out with any chromatography media in any mode. The intermediate chromatography step may employ any chromatography type, including column chromatography and membrane chromatography.

As further intermediate step or polishing step, also other chromatography types can be employed. For example, anion exchange column chromatography and anion exchange membrane chromatography may be employed as polishing step, most preferred being the flow-through mode. Another possibility is to apply hydroxyapatite chromatography, in particular ceramic hydroxyapatite in binding mode.

A first aspect of the invention refers to a method for prevention of precipitations in the course of a capture affinity chromatography of an immunoglobulin from a cell culture fluid, the method comprising the following steps in the following order:

(a) adding a flocculation-inducing compound to cell culture fluid;

(b) depth filtration of the mixture of step (a);

(c) exposing the filtrate obtained in step (b) to affinity chromatography, wherein the immunoglobulin is bound to the affinity chromatography medium;

(d) washing the affinity chromatography medium using a washing buffer with a pH value of 5 to 9 and a ionic strength of 0.1 to 5.0 mol/l; and (e) eluting the immunoglobulin from the affinity chromatography resin using an elution buffer with a pH value of 2.5 to 4.5.

Pre-Cleaning Step: Flocculation

In the experiments, which lead to the present invention it was observed that the cell-free harvest material (clarified supernatant) still contains several substances that, along with the immunoglobulin to be purified, bind strongly to the capture resin. This affects the re-use of the resin and the quality of the immunoglobulin after elution from the capture resin. This could be improved by an additional pre-cleaning chromatography based on anion exchange chromatography in a flow through mode (WO2015135884). Despite remarkable reduction of HCDNA and HCP levels, there was still a demand for further improvements. It was observed that the Protein A eluate still tends towards turbidity, which is caused by impurities rather than by the immunoglobulin itself. The low pH required for elution, the relative amount of impurities and the high protein concentrations promote the turbidity. Besides turbid elution pools also increased column backpressure was observed. The increased viscosity best explains this. In addition, the pre-cleaning anion exchange chromatography column is a disliked cost factor, due to a relatively large size required for the very high load of contaminants. The latter is enhanced by prolonged fermentation times required for higher mab titer and hence for economic production. Since the filter effect of the anion exchange resin is restricted mainly to the retention of negatively charged molecules and some of the turbidity-causing impurities still slip through, there was a demand for a simpler and more effective pre-capture cleaning strategy. According to the results of the present invention, the insertion of a suitable pre-cleaning flocculation method surprisingly represents a good solution for rapid and simple purification of the harvested culture fluid. By removal of further impurities, the developed flocculation method improves the purity of the sample, reduces critical contaminations, which promote the turbidity during low pH elution of the capture medium, and protects the costly affinity column. The flocculation method of the present invention is simple, rapid, without loss of product, and reasonably priced. Moreover, it turned out that the flocculation method can be performed either (i) before the cells are removed from the cell culture fluid, which means in presence of the cells, or (ii) after the cells were removed from the cell culture fluid, which means in absence of cells. The purity of the immunoglobulin before and after the Protein A step is comparable for both methods. By the former method the flocculated material, which comprises the cells, too, is separated by centrifugation and the supernatant is further clarified by a filtration train. In the latter method, the cells are precipitated by centrifugation and the supernatant undergoes flocculation. A filtration train then removes the flocculated material. The filtration train, in the simplest mode, consists of a depth filter. However, more preferred is a depth filter and a micro filter in series. In the course of scale-up to full scale production, the flocculation after cell separation turned out to be the method of choice. When the flocculation was performed directly in the cell culture the removal of the floc, comprising the whole cell mass, from the fermenter and from the separator was very time-consuming.

A high number of different flocculation methods using different flocculants were known and experimentally proven effective in the clarification of mammalian cell cultures expressing monoclonal antibodies. Most of the methods require a combination of substances and/or further manipulation of the culture fluid, e.g. pH adaption. Furthermore, many published methods utilize flocculation in place of the centrifugation step. In contrast, the present invention combines three methods for optimal clarification of the culture fluid in the following order: 1) Cell separation by centrifugation or filtration, 2) flocculation, and 3) depth filtration.

When the pH of the culture fluid is less than the pI of the antibody to be purified, the antibody carries net positive charge. Under these conditions, a cationic electrolyte may flocculate or precipitate impurities, residual cells and cell debris, and leave the antibody in solution. The floc can then be removed by centrifugation and/or depth filtration, optionally followed by microfiltration.

The present invention utilizes a single cationic compound, such as a divalent metal ion, a water-soluble organic polymer, or a water-insoluble organic polymer for inducing the flocculation. No further substances such as stimulus responsive polymers or salts are necessary for performing the flocculation step of this invention. Likewise, the flocculation method of the present invention is performed without further adjustment of pH or conductivity.

The term "in the following order" is to be understood to mean that the mentioned process steps are carried out in the listed order. Further process steps may be incorporated before, after and between the listed process steps.

The chromatography media may be disposable or reusable. In one embodiment the chromatography resin is reusable. In a specific embodiment the chromatography resins of step (b), (c), and (d) are reusable.

Chromatography media that are reusable, are cost-effective compared to chromatography media that are configured as disposables. In particular, for the capture chromatography large volumes of chromatography medium are used. Therefore, it is a particular advantage to use a reusable chromatography medium, e.g. a frequently reusable affinity chromatography resin for the capture step. The use of pre-cleaning steps of the present invention allow for certain downscaling of the expensive affinity capture column and for an increased lifetime and thus reduces the overall cost of goods.

The term "reusable" as used herein means that the medium or resin is configured to be reused for more than one purification cycle, i.e. at least 2, 5, 10, 50, 100, 200, 300, 400, 500 or more purification cycles. Between each cycle, the chromatography medium or resin may be washed and/or regenerated and/or sterilized and/or stored.

In a preferred embodiment the cationic compound used as flocculant is selected from a divalent metal ion salt, a water-soluble organic polymer and a water-insoluble organic polymer. More preferred are water-soluble organic polymers.

The divalent metal ion salt may be for example $CaCl_2$). The water-soluble organic polymer may be for example poly (diallyldimethylammonium chloride). The water-insoluble organic polymer may be for example chitosan. Even more preferably the flocculant is poly (diallyldimethylammonium chloride).

In one embodiment, the water-soluble organic polymer is applied with a final concentration of 0.01 to 1.0% (w/v), preferably of 0.02 to 0.15% (w/v), more preferably of 0.025 to 0.090% (w/v). In a preferred embodiment, the water-soluble organic polymer is added with a final concentration of 0.0375 to 0.075% (w/v). In a further preferred embodiment the water-soluble organic polymer is added with a final concentration of 0.015 to 0.05% (w/v).

In a preferred embodiment the water-soluble organic polymer used to induce flocculation is poly (diallyldimethylammonium chloride) with a molecular mass of 10 kDa to 10 000 kDa. In another preferred embodiment, the flocculation step is performed under stirring, at room temperature, for at least 10 min, for at least 15 min, or for at least 20 min, preferably for at least 30 min. Room temperature in the present invention means 15-25° C., 20-25°, preferably 18-22° C. Stirring means continuous agitation and/or stirring using suitable mechanical devices.

In a further preferred embodiment, the poly (diallyldimethylammonium chloride) starting solution added to the culture fluid for inducing the flocculation has a concentration of 5-15% (w/v), preferably 9-11% (w/v), more preferably 10% (w/v). Most preferred is a solution of neutral pH, having less than 0.1% diallylammonium chloride, having a microbial count of less than 10 CFU/ml, and being devoid of sodium chloride.

In one embodiment of the present invention, the flocculation step is performed before the cells are removed from the cell culture fluid by adding the flocculant directly to the fermenter at the end of the cultivation period. In other words, in such embodiments before the flocculation step no further centrifugation and/or filtration step takes place. The floc, including the cells, is then removed by sedimentation in a centrifuge, preferably in a disk stack centrifuge suitable for large volumes. The resulting supernatant can be further clarified by depth filtration, optionally followed by microfiltration.

In other embodiments, step (a) comprises the following steps:

(a1) centrifugation and/or filtration of the cell culture fluid; and (a2) adding a flocculation-inducing compound to the supernatant or filtrate obtained in step (a1).

In other words, the flocculation step is performed after the cells are removed from the cell culture fluid by adding the flocculant to the supernatant after a centrifugation and/or filtration step is performed.

Thus, in specific embodiments the method of the invention comprises the following steps in the following order:

(a1) centrifugation and/or filtration of the cell culture fluid;

(a2) adding a flocculation-inducing compound to the supernatant or filtrate obtained in step (a1);

(b) depth filtration of the mixture of step (a2);

(c) exposing the filtrate obtained in step (b) to affinity chromatography, wherein the immunoglobulin is bound to the affinity chromatography medium;

(d) washing the affinity chromatography medium using a washing buffer with a pH value of 5 to 9 and a ionic strength of 0.1 to 5.0 mol/l; and (e) eluting the immunoglobulin from the affinity chromatography resin using an elution buffer with a pH value of 2.5 to 4.5.

Preferably, the floc of step (a2) is removed by depth filtration, optionally followed by microfiltration.

Preferably, except poly (diallyldimethylammonium chloride) no further substances are added for performing the flocculation. In other words, in step (a) no further flocculation-inducing compounds except poly (diallyldimethylammonium chloride) are added.

Preferably, the flocculation with poly (diallyldimethylammonium chloride) is performed without further adjustment of pH or conductivity. This means in the flocculation step and the following filtration step(s) before affinity chromatography, in particular in the flocculation step (a2), the pH or conductivity is not adjusted.

Thus, in a specific embodiment, the method of the invention comprises the following steps in the following order:

(a1) centrifugation and/or filtration of the cell culture fluid;

(a2) adding a flocculation-inducing compound to the supernatant or filtrate obtained in step (a1);

(b) depth filtration of the mixture of step (a2);

(c) exposing the filtrate obtained in step (b) to affinity chromatography, wherein the immunoglobulin is bound to the affinity chromatography medium;

(d) washing the affinity chromatography medium using a washing buffer with a pH value of 5 to 9 and a ionic strength of 0.1 to 5.0 mol/l; and (e) eluting the immunoglobulin from the affinity chromatography resin using an elution buffer with a pH value of 2.5 to 4.5;

wherein except the poly (diallyldimethylammonium chloride) no further substances are added for performing the flocculation; and wherein the flocculation with poly (diallyldimethylammonium chloride) is performed without further adjustment of pH or conductivity.

Affinity Capture Chromatography Step: Protein A Chromatography

The term "capture step" is understood as the first chromatography step conducted in the binding mode. The capture step for purification of an immunoglobulin out of culture fluids is usually carried out as an affinity chromatography step. Protein A or derivatives or analogues thereof are mostly used as affinity capture. According the present invention affinity chromatography was successfully used to capture immunoglobulins. The term "affinity chromatography" for this invention means a method of selectively binding the immunoglobulin out of the culture fluid based on a highly specific interaction between a ligand and the immunoglobulin.

As used herein, the term "immunoglobulin binding protein/peptide affinity chromatography" refers to affinity chromatography which employs as ligands recombinant proteins of microbial origin (e.g. *Staphylococcus aureus, Streptococcus, Peptostreptococcus magnus*) or variants derived thereof, or synthetic peptides that may be of microbial origin with the ability to bind to immunoglobulins. Exemplary immunoglobulin binding proteins may be Protein A, Protein G, Protein L, or Protein A/G. Besides this binding proteins from microbial origin proteins or peptides derived from Fc gamma A receptor (FcR-IIIA) are exemplary affinity ligands, too. Preferably, the immunoglobulin binding protein or peptide is Protein A. The ligands can comprise one or more of the E, D, A, B and C domains of Protein A. More preferably the ligands comprise domain B of protein A or the engineered protein Z. An exemplary resin employing as ligand a 14 kD peptide recombinantly produced with *Saccharomyces cerevisiae* is the resin sold under the tradename IGSELECT™ (GE Healthcare). This ligand for which no further information is available was specifically designed for high affinity to all subclasses of human IgG-Fc.

By using a Protein A affinity chromatography step as the capture step after the pre-cleaning flocculation step the method of the invention provides a cost-effective immunoglobulin purification method while taking advantage of the significant binding specificity of Protein A affinity chromatography in the purification of immunoglobulins.

In a preferred embodiment, the invention provides a method for purifying an immunoglobulin from a sample comprising the immunoglobulin and at least one impurity, the method comprising the following steps in the following order:

(a) adding a flocculation-inducing compound to cell culture fluid;

(b) depth filtration of the mixture of step (a);

(c) exposing the filtrate obtained in step (b) to Protein A chromatography, wherein the immunoglobulin is bound to the Protein A chromatography medium;

(d) washing the Protein A chromatography medium using a washing buffer with a pH value of 5 to 9 and a ionic strength of 0.1 to 5.0 mol/l; and (e) eluting the immunoglobulin from the affinity chromatography resin using an elution buffer with a pH value of 2.5 to 4.5.

In a preferred embodiment, the Protein A chromatography resin used for the capture step comprises an alkali-tolerant Protein A derivative as a ligand, bound to highly cross-linked agarose. In a more preferred embodiment the alkali-tolerant Protein A derivative is an alkali-stabilized tetramer variant of domain B of Protein A.

In order to make the Protein A affinity chromatography resin more resistant to harsh cleaning conditions and to provide protection against inter-run cross-contamination effects, it is common today to use improved Protein A affinity resins, bearing ligands specially engineered to ensure alkali tolerance, high binding capacity, and low ligand leakage. One major draw back of these improved resins is, however, that they are significantly costlier than conventional Protein A resins. It is an important advantage of the method of the present invention that both conventional Protein A resins as well as the more recent new generation Protein A resin products can be used. Since the Protein A resins are exposed to a lower impurity burden, conventional and cheaper Protein A resins become acceptable despite their limitation to rather mild regeneration conditions. However, as a result of the pre-cleaning step of the invention and independently from the selected Protein A resin, both conventional and new generation resins can be used over a longer lifetime. Further, due to the fact that the cleaning of the Protein A column becomes easier, the process also becomes more economical.

Examples of common Protein A resins that can be used for the purpose of the invention may include, but are not limited to, those sold under the tradenames UNOSPHERE SUPRA™ (Bio-Rad), Protein A Ceramic HyperD F (Pall Corporation), POROS® MABCAPTURE® A (Applied Biosystems), PROSEP® HC, PROSEP® Ultra, and PROSEP® Ultra Plus (EMD Millipore), Protein A SEPHAROSE® FF, rProtein A SEPHAROSE® FF, rmp Protein A SEPHAROSE® FF, IGSELECT™, MABSELECT®, MABSELECT SURE®, MABSELECT SURE® LX, MABSELECT XTRA®, MABSELECT PRISMA® (GE Healthcare), PRAESTO® A, PRAESTO® AP, PRAESTO® APc, PRAESTO® Jetted A50) (Purolite Life Sciences) and TOYOPEARL® rProtein A (Tosoh Bioscience).

When used herein, the term "Protein A" encompasses Protein A recovered from a native source thereof, Protein A produced synthetically or biosynthetically (e.g. by peptide synthesis or by recombinant techniques), and variants thereof which retain the ability to bind proteins which have CH2/CH3 and/or Fc regions. Preferably, resins with high binding capacity and/or alkaline stability may be used. For example, Protein A, Protein A derivative, or alkali-stabilized Protein A-derived affinity medium may be used. Preferably, alkali-stabilized Protein A-derived (*E. coli, Saccharomyces cerevisiae*) ligands may be used. The alkali-stabilized, Protein A-derived ligand may be coupled to a highly cross-linked agarose matrix, preferably immobilized with a chemically stable thio-ether linkage. One example is the resin sold under the tradename MABSELECT SURE® from GE Healthcare Life Sciences, which can be rapidly and efficiently cleaned after the run with up to 0.5 M NaOH. The alkali-stabilized ligand of MABSELECT SURE® is derived from the B-domain of Protein A and essentially lacks the VH3 binding domain giving a higher elution pH. A preferred product is the resin sold under the tradename MABSELECT SURE® LX, which has a higher binding capacity than MABSELECT SURE®.

One or several wash steps between the sample load on the Protein A affinity column and the elution of the immunoglobulin from the Protein A column may be included employing special wash buffer(s). The wash buffer is the buffer used to remove impurities from the Protein A resin without removing significant amounts of the immunoglobulin of interest bound to the Protein A. The wash buffer may comprise salt and detergent (e.g. polysorbate); salt and solvent (e.g. hexylene glycol); high concentration salt (e.g. high molarity Tris buffer); or salt and polymer (e.g. polyethylene glycol). Furthermore, the wash buffer may include chaotropic reagents (e.g. urea or arginine) and/or protease inhibitors (e.g. EDTA). Finally, the wash buffer may have a lower pH as the loading buffer and/or a higher pH as the elution buffer.

For the elution of the immunoglobulin of interest from the Protein A column an elution buffer is applied. Preferably, the elution buffer has a low pH and thereby disrupts interactions between Protein A and the immunoglobulin of interest by changing the protein conformation. Preferably, the low pH elution buffer has a pH in the range from about 2 to about 5, most preferably in the range from about 3 to about 4. Examples of buffers that will control the pH within this range include phosphate, acetate, citrate, glycine, and ammonium buffers, as well as combinations of these.

Such preferred buffers are citrate and acetate buffers, most preferably sodium citrate or sodium acetate buffers. Other elution buffers are contemplated, including high pH buffers (e.g. those having a pH of 9 or more) or buffers comprising a compound or composition such as $MgCl_2$ (2 mM) for eluting the immunoglobulin of interest.

The Protein A affinity chromatography resin may be regenerated with 0.1 to 0.5 NaOH, preferably within the column (cleaning in place).

Intermediate/Polishing Chromatography Step: Cation Exchange Chromatography

The method as described herein may further comprise a cation exchange chromatography step.

Cation exchange chromatography relies on charge-charge interactions between the proteins in the sample and the charges immobilized on the resin. In cation exchange chromatography, the molecules to be bound are positively charged and the immobilized functional groups (ligands) are negatively charged. Commonly used cation exchange resins are S-resins, (sulphonate), SP resins (sulphopropyl), SiB resins (sulphoisobutyl), SE resins (sulphoethyl), and CM resins (carboxymethyl).

However, in general the cation exchange chromatography step can be performed with all common commercially available cation exchange resins or membranes. Cation exchange resins may be used in the form of pre-packed columns or membranes on which the functional group, e.g. sulfonic acid, is fixed. Alternatively, the resins may be purchased as bulk material and the columns packed by the user. There are no specific limitations as to the capacity and the dimension of the columns other than the usual ones. The person skilled in the art knows the amount of cation exchange resin and the size of the column to be used. This depends on the overall scale of the process.

Typical commercially available products include, for example, those chromatography resins sold under the tradenames MACRO-PREP® High S, MACRO-PREP® CM, UNOSPHERE™ Rapid S, UNOSPHERE™ Rapid S40, NUVIA® S, and NUVIA® HR-S (Bio-Rad, California, USA), TOYOPEARL® CM, TOYOPEARL® SP, TOYO-PEARL® Sulfate 650 F, and TOYOPEARL® GigaCap S (Tosoh Bioscience, Germany), MILLIPORE® PRORES™ S. FRACTOGEL® EMD COO—, FRACTOGEL® EMD SO3-, FRACTOGEL® EMD SE Hicap, ESHMUNO® CPX (Merck KGAA, Germany), BIOSEPRA™ CM Ceramic HyperD, BIOSEPRA™ S Ceramic HyperD, S HyperCel (Pall Corporation, New York, USA), POROS® HS, POROS® XS (Applied Biosystems, Germany), BioPro IEX SmartSep S, BioPro IEX S75 (YMC Europe), PRAESTO® SP, PRAESTO® Jetted SP35 (Purolite Life Sciences, Europe), CM-SEPHAROSE® FF, SP-SEPHAROSE® FF, S-SEPHAROSE® FF, SP-SEPHAROSE® HP, SP-SEP-HAROSE® XL, SP-SEPHAROSE® Big Beads, CM-SEP-HADEX®, CAPTO® S, CAPTO® SP ImpRes, and Source S (all GE Healthcare, Germany).

Commonly, cation exchange chromatography is performed using buffers at pH values between 4 and 7.

Preferred cation exchange resins of this invention are strong cation exchangers using sulfonate, sulfopropyl, or sulfoisobutyl ligands. Most preferred are sulfonate or sulfopropyl ligands linked to rigid matrices such as highly cross-linked agarose, e.g. in the resin sold under the tradename NUVIA® HR-S, or poly(styrenevinylbenzene), e.g. in the resin sold under the tradename POROS® 50 HS, or polymethacrylate, e.g. in the resin sold under the tradename FRACTOGEL® EMD SO3-. The most preferred cation exchange resin is the resin sold under the tradename POROS® HS 50 with sulfopropyl ($-CH_2CH_2CH_2SO_3^-$) ligands bound to a cross-linked poly(styrenedivinylbenzene) matrix.

The cation exchange chromatography may be equilibrated with a buffer having a pH of about pH 4 to about pH 8. The buffer concentration may be in the range of 10 mM to 100 mM, preferably in the range of 20 mM to 50 mM.

Examples of buffers used for cation exchange chromatography are citric acid, lactic acid, succinic acid, formic acid, butanedioic acid, acetic acid, malonic acid, glycine, MES, PIPES, phosphate, bistris, or mixtures thereof.

The cation exchange chromatography step may separate charge variants of the immunoglobulin and may deplete residual host cell proteins, DNA, aggregates, fragments, viruses, endotoxins, flocculants, and leached Protein A.

The immunoglobulin may bind to the resin at a pH value below the isoelectric point (pI) of the immunoglobulin and at low conductivity.

Isoelectric point or pI of a protein refers to the pH at which the protein has a net overall charge equal to zero, i.e. the pH at which the protein has an equal number of positives and negative charges. Determination of the pI may be accomplished according to techniques established in the prior art, such as isoelectric focusing.

Low conductivity means below 2 mS/cm.

For elution, an increase in the ionic strength of the elution buffer may be used, provided either by a single step or a gradient. Exemplary salts used in elution of cation exchange chromatography are chloride salts, sulfate salts, phosphate salts, citrate salts, formate salts, or acetate salts. Preferably, NaCl or KCl are used. The ionic strength may be increased to up to 1M.

Alternatively, an increase in the pH of the elution buffer may be used, provided either by a single step or a gradient.

A preferred embodiment for the performance of the cation exchange chromatography is a pH working range between 4 and 6, more preferably a pH range between 4.5 and 5.5. Either carbonic or amino acids as buffer substances may be used, citric acid or glycine being most preferred.

In a further preferred embodiment, the elution of immunoglobulin bound to the cation exchange resin is performed by a change in the pH value, i.e. an increase in pH. This may be achieved by a gradient from low pH to high pH provided by mixing of two different buffer solutions. Preferred are the citrate buffers for the low pH and phosphate buffers for the high pH. In a preferred embodiment, the pH gradient is formed by mixing a citrate buffer of about pH 5 to 6 with a phosphate buffer of about pH 7 to 9. The buffers may be prepared by using the sodium salts of the acids at a concentration of 10 to 50 mM. A preferred range for a pH gradient is between 5.0 and 7.5. In another preferred embodiment, the pH gradient is formed by mixing glycine buffers of pH 8.7 and pH 10.5. Optionally, the pH of the elution pool is adjusted, e.g. with acetic acid, before it is loaded on the final chromatography column.

Alternatively, an increase in both the pH and ionic strength of the elution buffer may be used for elution, provided either by a single step or a gradient.

In one embodiment the eluate of the Protein A chromatography is exposed to cation exchange chromatography.

Typically, the eluate of the Protein A chromatography will be exposed to a virus inactivation step followed by a cation exchange chromatography Thus, in some embodiments, the method of the invention may comprise the following steps in the following order:
- (a) adding a flocculation-inducing compound to cell culture fluid;
- (b) depth filtration of the mixture of step (a);
- (c) exposing the filtrate obtained in step (b) to affinity chromatography, wherein the immunoglobulin is bound to the affinity chromatography medium;
- (d) washing the affinity chromatography medium using a washing buffer with a pH value of 5 to 9 and a ionic strength of 0.1 to 5.0 mol/l;

(e) eluting the immunoglobulin from the affinity chromatography resin using an elution buffer with a pH value of 2.5 to 4.5;

(f) incubating the eluate of step (e) for virus inactivation at a low pH value of 2.5 to 4.5, for at least 10 minutes; and (g) performing a cation exchange chromatography.

The cation exchange chromatography resin may be regenerated with 1M NaCl for 3 to 5 column volumes. Further, a cleaning in place procedure may be applied comprising the following steps: (a) washing with 1 to 5 column volumes of 1M NaOH, 1M NaCl, (b) washing with 1 to 5 column volumes of 1M acetic acid or TFA, (c) re-equilibration.

Polishing Chromatography Step: Mixed-Mode Chromatography

The method of the invention may further comprise a mixed-mode chromatography step as polishing step, i.e. it is carried out in the sequence (as single or as one of several steps) after the affinity chromatography.

The media referred to as mixed-mode media or resins are chromatographic media possessing functional groups consisting of either charged hydrophobic ion exchange ligands or crystalline minerals such as hydroxyapatite or fluorapatite. Instead of "mixed-mode chromatography" the term "multi modal chromatography" or in connection with a specific procedure "hydrophobic charge induction chromatography" has sometimes been used. Mixed-mode chromatography is an interaction of at least two principles, hydrophobic interaction and ion exchange or metal affinity interaction and ion exchange. Mixed-mode chromatography provides less predictable selectivities that cannot be reproduced by a single mode chromatography method such as ion exchange or hydrophobic interaction chromatography, respectively. Positively charged hydrophobic ligands belong to the group of anion exchanger mixed-mode (for example in the anion exchanger sold under the tradename CAPTO®Adhere), and the negatively charged ligands belong to the cation exchanger mixed-mode (for example in the cation exchanger sold under the tradename CAPTO® MMC). Some mixed-mode media have zwitterionic character (for example Bakerbond ABx). Other mixed-mode media possess hydrophobic ligands which are ionisable and convert from uncharged to positively charged by lowering the pH (for example MEP HyperCel). Finally, hydroxyapatite and fluorapatite media have more complex mixed-mode functions by possessing positively charged calcium ions and negatively charged phosphate groups.

In a preferred embodiment the mixed-mode chromatography used as polishing step utilizes a resin having hydrophobic and anion exchange functions. More preferred are mixed-mode resins containing positively charged N-benzyl-N-methyl ethanolamine ligands, which are bound to a highly cross-linked agarose matrix.

In some embodiments, the method comprises the following steps in the following order:

(a) adding a flocculation-inducing compound to cell culture fluid;

(b) depth filtration of the mixture of step (a);

(c) exposing the filtrate obtained in step (b) to affinity chromatography, wherein the immunoglobulin is bound to the affinity chromatography medium;

(d) washing the affinity chromatography medium using a washing buffer with a pH value of 5 to 9 and a ionic strength of 0.1 to 5.0 mol/l;

(e) eluting the immunoglobulin from the affinity chromatography resin using an elution buffer with a pH value of 2.5 to 4.5;

(f) incubating the eluate of step (e) for virus inactivation at a low pH value of 2.5 to 4.5, for at least 10 minutes;

(g) performing a cation exchange chromatography; and (h) performing a mixed-mode chromatography.

Preferably, the mixed-mode chromatography step follows the cation exchange chromatography. More preferably, the mixed-mode chromatography step following the cation exchange chromatography is performed with medium comprising positively charged ligands. More preferably, the positively charged ligand is N-benzyl-N-methyl ethanol amine and the ligand is bound to highly cross-linked agarose.

The following conditions may be applied when loading the positively charged mixed-mode chromatography resin in the bind and elute mode: pH 6 to pH 9, preferably pH 7.0 to 8.5; conductivity 0.5 to 10 mS/cm, preferably 1 to 4 mS/cm. One or more washing steps may be used. The conditions depend on the pI of the immunoglobulin and can be specifically adjusted according the desired separation.

The most preferred mixed-mode resin used for polishing step (d) is the resin sold under the tradename CAPTO®Adhere (GE Healthcare Life Science).

The preferred loading conditions for the CAPTO®Adhere chromatography in binding mode may be as follows: The resin is equilibrated with 0.5M Na-phosphate, pH 8.2 followed by 20 mM Na-phosphate, pH 8.2. The sample (cation exchange pool) is adjusted to pH 8.0-8.5 and a conductivity of 1-4 mS/cm and loaded onto the column. After washing with the equilibration buffer 20 mM Na-phosphate, pH 8.2 the immunoglobulin of interest may be eluted from the CAPTO®Adhere resin, for example with 20 mM Na-phosphate, pH 5 to 7, preferentially pH 5.5 to 6.5.

Alternatively, the CAPTO®Adhere chromatography can be performed in the flow-through mode. Thereby, the pH and the ionic strength have to be adjusted in such a way that the immunoglobulin does not bind to the Mixed mode ligand while residual contaminants to be cleared (DNA, aggregates, leached Protein A, host cell proteins) remain bound. The conditions depend on the pI of the immunoglobulin. Preferably, phosphate or Tris buffers are used in a pH range of 6.5 to 8.5, more preferably between pH 7 and 8. Conductivity is adjusted with salt, such as NaCl or by the buffer concentration. Most preferred is a Na-phosphate buffer in the concentration range of 10 to 50 mM supplemented with NaCl in the concentration range of 50 to 200 mM. It has to be considered that high salt concentrations, although desorbing the ionic interaction, promote a hydrophobic interaction with the ligand.

The regeneration (cleaning in place) for the mixed-mode resin may be performed with low pH, high salt, and high pH, e.g. with 10 to 200 mM citric acid, 0.5-2M NaCl, and 10 mM to 1M NaOH.

The preferred regeneration procedure is performed by washing consecutively with solutions A-D: Solution A: 100 mM citric acid, 2M NaCl; Solution B: 2M NaCl: Solution C: 1M NaOH; Solution D: 10 mM NaOH. The storage of the resin may be performed in Solution D.

In a further preferred embodiment, the method of the invention comprises the following steps in the following order:

adding a flocculation-inducing compound to cell culture fluid;

depth filtration;

affinity chromatography, wherein the immunoglobulin is bound to the affinity chromatography medium;

washing the affinity chromatography medium using a washing buffer with a pH value of 5 to 9 and a ionic strength of 0.1 to 5.0 mol/l;

eluting the immunoglobulin from the affinity chromatography resin using an elution buffer with a pH value of 2.5 to 4.5; and strong cation exchange chromatography, wherein the immunoglobulin is bound to the strong cation exchange chromatography resin, and obtaining the immunoglobulin in the eluate by desorbing the immunoglobulin from the strong cation exchange chromatography resin; and positively charged mixed-mode chromatography; wherein the resin is equilibrated with phosphate buffer of pH 8 to 8.5, the immunoglobulin is bound to the positively charged mixed-mode chromatography resin, and the elution of the immunoglobulin is performed with phosphate buffer of pH 5 to 7.

Polishing Chromatography Step: Anion Exchange Chromatography

The method of the invention may further comprise an anion exchange chromatography step as polishing step, i.e. it is carried out in the sequence (as single or as one of several steps) after the affinity chromatography.

The media referred to as anion exchange media or resins are chromatographic media possessing functional groups consisting of positively charged ion exchange ligands. The anion exchange chromatography medium may be a strong or a weak anion exchange chromatography medium, including anion exchange membranes.

In anion exchange chromatography the molecules to be bound are negatively charged and the immobilized functional groups (ligands) are positively charged. Commonly used anion exchange chromatography media are Q media, (quaternary amine ligands), TMAE resins (trimethylaminoethyl ligands), and DEAE resins (diethylaminoethyl ligands). However, in general the anion exchange chromatography step can be performed with all common commercially available anion exchange media. Anion exchange media may be used in the form of pre-packed columns or as membranes. Alternatively, the resins may be purchased as bulk material and the columns packed by the user. There are no specific limitations as to the capacity and the dimensions of the columns other than the usual ones. The person skilled in the art knows the amount of anion exchange chromatography medium and the size of the column to be used. This depends on the overall scale of the process.

In particular, strong anion exchange chromatography media have been found to be effective in removing the residual impurities.

Preferably, strong anion exchange chromatography media comprising a ligand selected from the group consisting of quaternary aminoethyl (QAE) moieties, quaternary ammonium moieties and trimethylammonium moieties are used.

Typical strong anion exchange chromatography media that can be used for the purpose of the invention comprise functional groups such as: quaternary aminoethyl (QAE) moieties, resins include e.g. the resins sold under the tradenames TOYOPEARL®QAE (available from Tosoh Bioscience, Germany), Selectacel QAE (a quaternary aminoethyl derivative of cellulose, available from Polysciences Inc., Pennsylvania USA), QAE SEPHADEX® (available from GE Healthcare, Germany), and others; quaternary ammonium (Q) moieties, resins include e.g. resins sold under the tradenames Q SEPHAROSE® XL, Q SEPHAROSE® FF, Q SEPHAROSE® HP, Q SEPHAROSE® CL-4B, Q SEPHAROSE® Big Beads, Source Q, Resource Q, CAPTO® Q, CAPTO® Q ImPres (all available from GE Healthcare, Germany), POROS® HQ (Applied Biosystems, Germany), Q HyperCel, BIOSEPRA™ Q Ceramic HyperD (available from Pall Corporation, New York, USA) MACRO-PREP® High Q (Bio-Rad, California, USA), TOYOPEARL® Super Q (available from Tosoh Biosciences, Germany), UNOSPHERE™ Q (available from Bio-Rad, California, USA), BioPro IEX SmartSep Q (YMC Europe), PRAESTO® Q, PRAESTO® Jetted Q35 (Purolite Life Sciences, Europe); trimethylammoniumethyl (TMAE) moieties, resins include e.g. resins sold under the tradename FRACTOGEL® EMD TMAE (Merck KgaA, Germany); and trimethylammonium moieties, resins include e.g. resins sold under the tradename NUVIA® Q (available from Bio-Rad, California, USA).

More preferably, the anion exchange chromatography may be a strong anion exchange chromatography which is performed using a strong anion exchange chromatography resin having —$N(CH_3)_3^+$ (trimethylammonium) bound to highly cross-linked agarose (e.g. CAPTO® Q available from GE Health Care, Germany), or a medium having similar characteristics.

In some embodiments, the method comprises the following steps in the following order:

(a) adding a flocculation-inducing compound to cell culture fluid;

(b) depth filtration of the mixture of step (a);

(c) exposing the filtrate obtained in step (b) to affinity chromatography, wherein the immunoglobulin is bound to the affinity chromatography medium;

(d) washing the affinity chromatography medium using a washing buffer with a pH value of 5 to 9 and a ionic strength of 0.1 to 5.0 mol/l;

(e) eluting the immunoglobulin from the affinity chromatography resin using an elution buffer with a pH value of 2.5 to 4.5;

(f) incubating the eluate of step (e) for virus inactivation at a low pH value of 2.5 to 4.5, for at least 10 minutes;

(g) performing a cation exchange chromatography; and (h) performing an anion exchange chromatography.

Another preferred embodiment comprises an anion exchange chromatography in flow through mode subsequent to a cation exchange chromatography step in binding mode.

Thus, a preferred embodiment of the present invention provides a method with the following steps in the following order:

adding a flocculation-inducing compound to cell culture fluid;

depth filtration;

affinity chromatography, wherein the immunoglobulin is bound to the affinity chromatography medium;

washing the affinity chromatography medium using a washing buffer with a pH value of 5 to 9 and a ionic strength of 0.1 to 5.0 mol/l;

eluting the immunoglobulin from the affinity chromatography resin using an elution buffer with a pH value of 2.5 to 4.5; and strong cation exchange chromatography, wherein the immunoglobulin is bound to the strong cation exchange chromatography resin, and obtaining the immunoglobulin in the eluate by desorbing the immunoglobulin from the strong cation exchange chromatography resin; and strong anion exchange chromatography; wherein the immunoglobulin is not bound to the strong anion exchange chromatography resin, and obtaining the immunoglobulin in the flow through.

The most preferred anion exchange chromatography resin is CAPTO® Q (GE Health Care, Germany). The preferred loading conditions for the CAPTO® Q chromatography in flow through mode may be as follows: The resin is equilibrated with 25 mM Tris buffer pH 8 and the chromatography is performed with the same buffer.

The preferred regeneration procedure is performed by washing consecutively with solutions A-C: Solution A: 2M NaCl; Solution B: 1M NaOH; Solution C: 10 mM NaOH. The storage of the resin may be performed in Solution C.

Depth Filtration

Further, the method of the invention may comprise one or more depth filtration steps. In contrast to membrane filters, which separate by retaining the particles on the surface of a membrane, depth filters consist of a matrix of fibers or beads, wherein separation takes place throughout the matrix rather than on its surface.

Examples of depth filters include, but are not limited to, series of filters sold under the tradenames PALL® SCL (e.g. SXLP700416 and SXLPDE2408SP filter capsules, PALL® HP (e.g. PDD1, PDE2, PDH4, PDK5, PEKM) (Pall Corporation), MILLISTAK® (e.g. XOHC, FOHC, DOHC, A1HC, and B1HC Pod filters), HC-Pro, CLARISOLVE® (e.g. 40 MS) (EMD Millipore), or Zeta Plus (90ZB08, 30ZA/60ZA, 60ZN90ZA, delipid, VR07, and VR05 filter capsules) (3M).

Preferably, the depth filter is composed of pre-extracted inorganic filter aid, cellulose and a resin system that imparts a strong positive charge to the filter matrix, as for example Zeta Plus from 3M, United Kingdom.

Another preferred filter module is the purifier sold under the tradename EMPHAZE® AEX Hybrid purifier (3M) which is a depth filter with anion exchange functions.

Most preferred depth filters used for this invention are the filter capsules of the PDE2, PDH4 and P700 series from Pall Corporation.

The process parameters for performing the depth filtration comprise a volumetric load of 100 to 2000 L/m², preferably 200 to 1500 L/m2, more preferably below 1200 L/m² and most preferably 400 to 1000 L/m², a pressure of 0.2 to 2.0 bar, preferably 0.4 to 0.6 bar and room temperature.

In a further embodiment, the purification may include one or more filtration steps preceding the first chromatography step. In a preferred embodiment, the purification may include one centrifugation step and one or more filtration steps. In another preferred embodiment, the first chromatography step is preceded by a depth filtration and a microfiltration step performed after flocculation. In a more preferred embodiment, the first chromatography step is preceded by a cell separation step, a flocculation step, a depth filtration step and a microfiltration step.

Additional filtration steps using positively and/or negatively charged membranes may be included in a filtration train clarifying the sample after the flocculation and prior to the capture chromatography step. Filter modules, combining different materials, charged and uncharged, are also comprised in a preferred embodiment Preferably, the depth filtration filter comprises more than one layer. For example, a double-layer filter may be used for depth-filtration.

Ultrafiltration, Virus Filtration, Microfiltration

Further, the method of the invention may comprise one or more microfiltration, ultrafiltration and/or nanofiltration steps. Ultrafiltration is a form of membrane filtration in which pressure forces a liquid against a semipermeable membrane. Suspended solids and solutes of high molecular weight are retained, while water and low molecular weight solutes pass through the membrane. Ultrafiltration is a commonly used method for separation, purifying and concentrating macromolecular solutions, especially protein solutions. Ultrafiltration may be combined with diafiltration. This mode is suitable for buffer exchange, to remove salts and other microspecies from the solution via repeated or continuous dilution and re-concentration. Ultrafiltration may be performed with stacked membranes in a tangential flow or cross flow filtration system (TFF or TF-UF), especially for processing large sample volumes. Alternatively, hollow fiber systems are commonly used for ultrafiltration. Membrane cut-off sizes range from about 1 to 300 kD. For immunoglobulins, typical cut offs for the ultrafiltration membranes are 10-100 kD. Within the framework of the present invention, a molecular weight cut off of 30 or 50 kD for the UF membranes is preferred.

Microfiltration is a particle filtration method using membranes with pore sizes from about 0.1 to 10 μm. For sterile filtration, which puts special requirements on the environment, sterilized micro filters are used with pore sizes of about 0.2 μm. The use of additional pre-filters with larger pore sizes (0.45 μm, 3 μm) is common. This prevents the decrease in flow by rapid blocking of the small pore sized filters.

Finally, in biopharmaceutical production nanofiltration is predominantly used for viral filtration and is required for the safety of therapeutic proteins produced in mammalian cell cultures. Nanofiltration steps are usually performed at the end of downstreaming close to filling of the bulk of purified immunoglobulin. The pore sizes of the frequently used nanofilters range between 15 and 35 nm (in filters sold under the tradename PLANOVA®, Asahi Kasei, Japan; or VIRESOLVE®, EMD Millipore, Germany).

Within the scope of this invention, the terms "nanofiltration" and "virusfiltration" are used synonymously.

The present invention provides a further method for purifying an immunoglobulin from a cell culture fluid comprising the immunoglobulin and at least one impurity, the method comprising the following steps in the following order:

centrifugation and/or filtration of the cell culture fluid;

adding a flocculation-inducing compound to the supernatant or filtrate;

depth filtration;

microfiltration;

affinity chromatography, wherein the immunoglobulin is bound to the affinity chromatography medium;

washing the affinity chromatography medium using a washing buffer with a pH value of 5 to 9 and a ionic strength of 0.1 to 5.0 mol/l; and eluting the immunoglobulin from the affinity chromatography resin using an elution buffer with a pH value of 2.5 to 4.5.

In a preferred embodiment of the invention, the process of purification comprises one or more ultrafiltration/diafiltration and/or nanofiltration steps. These filtration steps can be performed using commercially available filtration devices, e.g. available from Pall Corporation, GE Healthcare, EMD Millipore, or Sartorius.

In a further embodiment, the method comprises a further step of exposing the eluate obtained from the affinity chromatography or the polishing step, or a composition derived therefrom and obtained after one or more further processing steps performed after said chromatography step to nanofiltration. Preferably, filters which are capable of retaining parvoviruses, most preferably with pore sizes of 15-35 nm, may be applied for the nanofiltration.

In some embodiments, the present invention provides a method for purifying an immunoglobulin from a cell culture fluid comprising the immunoglobulin and at least one impurity, the method comprising the following steps in the following order:

adding a flocculation-inducing compound to cell culture fluid;

depth filtration;

affinity chromatography, wherein the immunoglobulin is bound to the affinity chromatography medium;

washing the affinity chromatography medium using a washing buffer with a pH value of 5 to 9 and a ionic strength of 0.1 to 5.0 mol/l;

eluting the immunoglobulin from the affinity chromatography resin using an elution buffer with a pH value of 2.5 to 4.5;

cation exchange chromatography, wherein the immunoglobulin is bound to the cation exchange chromatography resin, and obtaining the immunoglobulin in the eluate by desorbing the immunoglobulin from the cation exchange chromatography resin;

mixed mode chromatography, wherein the immunoglobulin is either bound to the mixed mode chromatography resin, and obtaining the immunoglobulin in the eluate by desorbing the protein from the mixed mode chromatography resin, or not bound to the mixed mode chromatography resin, and obtaining the immunoglobulin in the flow through; and filtration of the eluate through a virus filter, optionally followed by a ultrafiltration/diafiltration step.

In further embodiments, the present invention provides a method for purifying an immunoglobulin from a cell culture fluid comprising the immunoglobulin and at least one impurity, the method comprising the following steps in the following order:

adding a flocculation-inducing compound to cell culture fluid;

depth filtration;

affinity chromatography, wherein the immunoglobulin is bound to the affinity chromatography medium;

washing the affinity chromatography medium using a washing buffer with a pH value of 5 to 9 and a ionic strength of 0.1 to 5.0 mol/l;

eluting the immunoglobulin from the affinity chromatography resin using an elution buffer with a pH value of 2.5 to 4.5;

cation exchange chromatography, wherein the immunoglobulin is bound to the cation exchange chromatography resin, and obtaining the immunoglobulin in the eluate by desorbing the immunoglobulin from the cation exchange chromatography resin;

anion exchange chromatography, wherein the immunoglobulin is not bound to the anion exchange chromatography resin, and obtaining the immunoglobulin in the flow through; and filtration of the eluate through a virus filter, optionally followed by a ultrafiltration/diafiltration step.

In a preferred embodiment, the invention provides a method for purifying an immunoglobulin from a cell culture fluid comprising the immunoglobulin and at least one impurity, the method comprising the following steps in the following order:

adding a flocculation-inducing compound to cell culture fluid;

depth filtration of the mixture;

exposing the filtrate to affinity chromatography, wherein the immunoglobulin is bound to the affinity chromatography medium;

washing the affinity chromatography medium using a washing buffer with a pH value of 5 to 9 and a ionic strength of 0.1 to 5.0 mol/l;

eluting the immunoglobulin from the affinity chromatography resin using an elution buffer with a pH value of 2.5 to 4.5;

cation exchange chromatography, wherein the immunoglobulin is bound to the cation exchange chromatography resin, and obtaining the immunoglobulin in the eluate by desorbing the protein from the cation exchange chromatography resin;

mixed mode chromatography, wherein the immunoglobulin is bound to the mixed mode chromatography resin, and obtaining the immunoglobulin in the eluate by desorbing the protein from the mixed mode chromatography resin;

nanofiltration; and ultrafiltration/diafiltration.

In further preferred embodiments, the present invention provides a method for purifying an immunoglobulin from a cell culture fluid comprising the immunoglobulin and at least one impurity, the method comprising the following steps in the following order:

adding a flocculation-inducing compound to cell culture fluid;

depth filtration;

affinity chromatography, wherein the immunoglobulin is bound to the affinity chromatography medium;

washing the affinity chromatography medium using a washing buffer with a pH value of 5 to 9 and a ionic strength of 0.1 to 5.0 mol/l;

eluting the immunoglobulin from the affinity chromatography resin using an elution buffer with a pH value of 2.5 to 4.5;

cation exchange chromatography, wherein the immunoglobulin is bound to the cation exchange chromatography resin, and obtaining the immunoglobulin in the eluate by desorbing the immunoglobulin from the cation exchange chromatography resin;

anion exchange chromatography, wherein the immunoglobulin is not bound to the anion exchange chromatography resin, and obtaining the immunoglobulin in the flow through; and nanofiltration; and ultrafiltration/diafiltration.

Virus Inactivation

Virus removal and/or inactivation are required for the production process of a recombinant protein drug such as a monoclonal antibody produced by cell culture, because of concerns about accidental contamination with viruses from raw materials or production steps. As a result, there is a considerable regulatory demand for the viral safety of every manufacturing process, which results in a biological therapeutic protein derived from cell cultures.

A viral inactivation step takes place after the affinity capture chromatography by keeping the eluate at low pH. Advantage is taken of the low pH elution from the affinity matrix. In such an aqueous acid environment many viruses, especially those of the enveloped type, are instable and disintegrate.

Low pH means pH values between 2 and 5, preferably between 2.5 and 4.5, more preferably between 3 to 4.

In a preferred embodiment the incubation time for virus inactivation is 10 min to 2 hours, more preferred 30 min to 90 min, most preferred 45 min to 75 min.

In a preferred embodiment virus inactivation is performed at room temperature under stirring and the pH is raised after the incubation.

The present invention provides a method for purifying an immunoglobulin from a cell culture fluid comprising the immunoglobulin and at least one impurity, the method comprising the following steps in the following order: (a1) separating the cells from the cell culture fluid by sedimentation;

(a) adding a flocculation-inducing compound to cell culture fluid;

(b) depth filtration of the mixture of step (a);

(c) exposing the filtrate obtained in step (b) to affinity chromatography, wherein the immunoglobulin is bound to the affinity chromatography medium;

(d) washing the affinity chromatography medium using a washing buffer with a pH value of 5 to 9 and a ionic strength of 0.1 to 5.0 mol/l;

(e) eluting the immunoglobulin from the affinity chromatography resin using an elution buffer with a pH value of 2.5 to 4.5;

(f) incubating the eluate of step (e) for virus inactivation at low pH of 2.5 to 4.5 for at least 10 minutes;

(g) exposing the eluate after virus inaction in step (f), or a composition derived therefrom and obtained after one or more further processing steps performed after step (f), to cation exchange chromatography, wherein the immunoglobulin is bound to the cation exchange chromatography resin, and obtaining the immunoglobulin in the eluate by desorbing the protein from the cation exchange chromatography resin;

(h) exposing the eluate obtained in step (g), or a composition derived therefrom and obtained after one or more further processing steps performed after step (g), to mixed mode chromatography, wherein the immunoglobulin is bound to the mixed mode chromatography resin, and obtaining the immunoglobulin in the eluate by desorbing the protein from the mixed mode chromatography resin;

(i) exposing the eluate obtained in step (h) or a composition derived therefrom and obtained after one or more further processing steps performed after step (h) to nanofiltration; and (j) exposing the filtrate of step (i) or a composition derived therefrom and obtained after one or more further processing steps performed after step (i) to ultrafiltration/diafiltration.

In a further embodiments step h) is as follows:

(h) exposing the eluate obtained in step (g), or a composition derived therefrom and obtained after one or more further processing steps performed after step (g), to mixed mode chromatography, wherein the immunoglobulin is not bound to the mixed mode chromatography resin, and obtaining the immunoglobulin in the flow through from the mixed mode chromatography resin.

Or, alternatively, instead of mixed mode chromatography anion exchange chromatography can be used and step h) is as follows:

(h) exposing the eluate obtained in step (g), or a composition derived therefrom and obtained after one or more further processing steps performed after step (g), to anion exchange chromatography, wherein the immunoglobulin is not bound to the anion exchange chromatography resin, and obtaining the immunoglobulin in the flow through from the anion exchange chromatography resin.

In a preferred embodiment the ultrafiltration/diafiltration is the last step of the purification of the immunoglobulin and no further chromatographies to step (c), (g), and (h) take place.

EXAMPLES

The methods of the invention for purifying immunoglobulins are supported and illustrated by reference to the following examples. It has to be emphasized that these examples should by no means be construed as limiting the scope of the invention.

Example 1: Immunoglobulins and Cell Cultures

The methods of the invention depend neither on specific antibodies nor on specific host cells used for the expression of the immunoglobulins. The same is true for the mode of expression and the selected culture conditions, which were optimized for maximum yields in the harvest. Different monoclonal antibodies were used during the development of the methods of the invention. They were successfully purified in various scales according to the methods of the invention. Most of the selected experiments presented in the Tables were performed with Bevacizumab, a humanized, anti-VEGF, IgG1 antibody. In addition, some other experiments were performed with Trastuzumab, a humanized, anti-HER2, IgG1 antibody and with Denosumab, a fully human anti-RANKL IgG2 antibody. All three antibodies were recombinantly expressed in CHO cells, which were propagated in fed-batch cultures of different scales. Most of the flocculation experiments in the development phase were performed with culture fluids from a laboratory scale of 10 L or a pilot scale of 100 L or 200 L. The production scale and maximum culture volume used in the examples was 5000 L. Some experiments were performed using a smaller production scale of 1000 L. Unless specified otherwise, the scale always refers to the culture volume.

Example 2: Comparing Different Flocculants
(Tables 1 to 3)

The flocculation experiments of Tables 1 to 3 were performed in different series using pilot scale (100 L) culture of CHO cells producing a humanized antibody of the IgG1 subclass (Bevacizumab). The titer of the antibody was between 1.16 and 1.52 g/L. The flocculants were added to 20 ml aliquots of the cell culture broth at the end of fermentation, before cell separation. Three different cationic substances were tested in different concentrations. 1) pDADMAC=poly (diallyldimethylammonium chloride), 2) chitosan, and 3) calcium chloride. pDADMAC was purchased as 10% (w/v) solution (EMD Millipore). Chitosan was purchased as solid substance (Sigma) and 1% (w/v) was solved in 0.1 M acetic acid. The pH operation range of chitosan is about 4.5 to 5.0. Calcium chloride was added using an aqueous stock solution.

The experiments were performed according the following sequence of steps:

Collecting an aliquot of 20 ml from the fermentation broth

Adding the flocculant

Incubation for 15 min at room temperature under stirring

Centrifugation at 4600 rpm/10 min (Thermo Scientific Table Centrifuge)

Microfiltration (PVDF, 0.2 μm, EMD Millipore)

Analysis for turbidity, HCDNA, and HCP

In order to evaluate the direct effect of the different flocculants in different concentrations a depth filtration was not performed. The centrifugation step removes floc, cells and cell debris. The subsequent microfiltration removes remaining particles. For the controls (zero values), no flocculant was added and no incubation took place. However, samples were centrifuged and filtered prior to analysis. A Protein A-based HPLC method determined the antibody concentrations.

TABLE 1a

Effect of flocculation with pDADMAC on reduction of HCDNA and turbidity pDADMAC

| Conc. [% w/v] | 0 | 0.0250 | 0.0375 | 0.0750 | 0.0900 |
|---|---|---|---|---|---|
| HCDNA [ng/ml] | 62900 | 59.9 | 16.0 | 16.0 | 16.0 |
| Reduction [%] | 0 | 99.91 | 99.98 | 99.98 | 99.98 |
| Turbidity [FNU] | 19.90 | 10.30 | 3.20 | 2.55 | 2.46 |
| Reduction [%] | 0 | 48.24 | 83.92 | 87.19 | 87.64 |

TABLE 1b

Effect of flocculation with chitosan on reduction of HCDNA and turbidity Chitosan

| Conc. [% w/v] | 0 | 0.025 | 0.050 | 0.075 | 0.200 | 0.400 |
|---|---|---|---|---|---|---|
| HCDNA [ng/ml] | 62900 | 32700 | 24200 | 20700 | 6690 | 5380 |
| Reduction [%] | 0 | 48.01 | 61.53 | 67.09 | 89.36 | 91.45 |
| Turbidity [FNU] | 19.90 | 17.60 | 17.30 | 17.10 | 16.1 | 16.3 |
| Reduction [%] | 0 | 11.56 | 13.07 | 14.07 | 19.10 | 18.09 |

TABLE 1c

Effect of flocculation with CaCl$_2$ on reduction of HCDNA and turbidity Calcium chloride

| Conc. [mM] | 0 | 40 | 50 | 60 | 70 | 80 | 100 | 120 |
|---|---|---|---|---|---|---|---|---|
| HCDNA [ng/ml] | 62900 | 21000 | 12000 | 1330 | 590 | 318 | 130 | 56.4 |
| Reduction [%] | 0 | 66.61 | 80.92 | 97.89 | 99.06 | 99.49 | 99.79 | 99.91 |
| Turbidity [FNU] | 19.90 | 11.20 | 14.60 | 13.20 | 11.70 | 10.50 | 7.86 | 7.40 |
| Reduction [%] | 0 | 43.72 | 26.63 | 33.67 | 41.21 | 47.24 | 60.50 | 62.81 |

Tables 1a to 1c show the results of the flocculation on the reduction of HCDNA and turbidity using three different flocculants. HCDNA was determined by Quant-iT™ High-Sensitivity dsDNA Assay Kit (Thermo Fisher) and qPCR (PrepSEQ™ Residual DNA Sample Preparation Kit and resDNASEQ™ Quantitative CHO DNA Kit, Thermo Fisher). The turbidity measurements were performed in a Hach Turbidimeter 2100Q and expressed as Formazin Nephelometric Units (FNU). The instrument is measuring scattered light from the sample at a 90-degree angle from the incident infrared light.

Table 1a shows the effect of pDADMAC up to 0.09% (w/v). Already with the lowest concentration (0.025% w/v) HCDNA was nearly completely removed (reduction 99.9%, three orders of magnitude). A turbidity reduction of 87% could be reached with 0.075% (w/v) pDADMAC. A further decrease of turbidity could not be reached with higher pDADMAC concentration in this experiment.

The results with chitosan as shown in Table 1b disclosed an effective HCDNA removal however at higher concentrations as required for pDADMAC. About 91.5% reduction was obtained at 0.4% (w/v). With respect to reduction of turbidity, not more than 19% reduction was measured.

The results of the CaCl$_2$) experiments are shown in Table 1c. Also for this flocculant, a very effective HCDNA reduction was obtained. A 99% reduction was measured at 70 mM and a 99.9% reduction at 120 mM CaCl$_2$). The reduction of turbidity was greater as for chitosan but lower as for pDADMAC. About 63% reduction at 120 mM could be achieved. Higher CaCl$_2$) concentrations were not tested.

Conclusions (Tables 1a to c): The initial concentration of HCDNA (i.e. controls without flocculation) was 62.9 μg/ml cell culture supernatant and 51.1 mg/g IgG, respectively. A loss of total protein or of antibody was not detectable for all flocculants and concentrations tested. Likewise, no increased cell rupture caused by the flocculation was observed. Surprisingly it is evident, that HCDNA contributes little, if at all, to the turbidity. For instance with 0.4% (w/v) chitosan about 91.5% of HCDNA was flocculated and removed whereas the turbidity was hardly reduced and remained at 82% of the control (Table 1b). For reducing both, HCDNA and turbidity, the flocculant pDADMAC is superior.

TABLE 2a

Effect of flocculation with pDADMAC on reduction of HCP pDADMAC

| Conc. [% w/v] | 0 | 0.0250 | 0.0375 | 0.0500 | 0.0750 | 0.0900 |
|---|---|---|---|---|---|---|
| HCP [μg/ml] | 2310 | 2280 | 2240 | 2170 | 2100 | 2060 |
| Reduction [%] | 0 | 1.30 | 3.03 | 6.06 | 9.09 | 10.82 |

TABLE 2b

Effect of flocculation with chitosan on reduction of HCP

Chitosan

| Conc. [% w/v] | 0 | 0.025 | 0.050 | 0.075 | 0.100 | 0.200 | 0.400 |
|---|---|---|---|---|---|---|---|
| HCP [μg/ml] | 1720 | 1670 | 1720 | 1720 | 1590 | 1580 | 1610 |
| Reduction [%] | 0 | (0) | 0 | 0 | 7.56 | 8.14 | 6.40 |

TABLE 2c

| Effect of flocculation with calcium chloride on reduction of HCP | | | | | |
|---|---|---|---|---|---|
| Calcium chloride | | | | | |
| Conc. [mM] | 0 | 10 | 20 | 50 | 60 | 70 |
| HCP [µg/ml] | 1410 | 1330 | 1200 | 1080 | 1080 | 1000 |
| Reduction [%] | 0 | 5.67 | 14.89 | 23.40 | 23.40 | 29.08 |

Tables 2a to 2c show the results of the flocculation on the reduction of HCP using three different flocculants. HCP was measured by using the CHO HCP ELISA Kit, 3G (Cygnus technologies).

Table 2a shows the effect of pDADMAC on the removal of HCP. Even with the highest concentration tested (0.09% w/v) the reduction was about 10.8% only.

As shown in Table 2b the effect of chitosan as flocculant on the reduction of HCP was insignificant. The best reduction was measured to be about 8.1% at 0.2% (w/v).

A better reduction of HCP was obtained in the CaCl$_2$) experiments as shown in Table 2c. A 29.1% reduction was measured at 70 mM. Higher concentrations may result in better reduction, however were not tested.

Conclusions (Tables 2a to c); The initial concentrations of HCP were between 1.4 and 2.3 mg/ml. By mass this is about 20-fold to 40-fold higher than the load of HCDNA. Again, it is obvious that also HCP contributes little to turbidity. For example 0.075% (w/v) pDADMAC reduces turbidity by about 87% (Table 1a), while the reduction of HCP was about 9% only (Table 2a). For reducing HCP by flocculation, CaCl$_2$) was superior. Tables 3a to 3c below summarizes the favourable concentrations of the three flocculants tested for reduction of HCDNA, turbidity, and HCP.

TABLE 3a

| Favorable concentrations of different flocculants for reduction of HCDNA | | |
|---|---|---|
| Flocculant | Concentration | Reduction |
| pDADMAC | 0.025% w/v | 99.9% |
| Chitosan | 0.400% w/v | 91.5% |
| CaCl$_2$ | 70 mM | 99.1% |

TABLE 3b

| Favorable concentrations of different flocculants for reduction of turbidity | | |
|---|---|---|
| Flocculant | Concentration | Reduction |
| pDADMAC | 0.075% w/v | 87.2% |
| Chitosan | 0.200% w/v | 19.1% |
| CaCl$_2$ | 120 mM | 62.8% |

TABLE 3c

| Favorable concentrations of different flocculants for reduction of HCP | | |
|---|---|---|
| Flocculant | Concentration | Reduction |
| pDADMAC | 0.090% w/v | 10.8% |
| Chitosan | 0.200% w/v | 8.1% |
| CaCl$_2$ | 70 mM | 29.1% |

All three flocculants were able to remove efficiently HCDNA due to their cationic nature. Since the initial problem of the current invention was mainly related to the turbidity observed in Protein A elution pools, pDADMAC was selected as the most suitable flocculant. This polymer can be used at lower concentrations and surprisingly results in nearly total removal of HCDNA in already the lowest concentration tested.

Example 3: Further Flocculation Experiments with pDADMAC (Tables 4 to 6)

In subsequent more extended test series, the effect of pDADMAC on the reduction of HCDNA and turbidity was investigated in parallel experiments using samples from six different cell cultures expressing Bevacizumab. The test methods were the same as described for Example 2. The ranges of the non-flocculated supernatants (controls) were 44.3 to 62.9 µg/ml HCDNA, 19.9 to 29.1 FNU turbidity, and 1.24 to 2.14 mg/ml HCP. The antibody titer were between 1.16 and 1.52 mg/ml. Five different pDADMAC concentrations were tested and the mean values of the reduction in % were calculated.

TABLE 4a

| Effect of pDADMAC concentration on reduction of HCDNA in different cell culture batches | | | | | | |
|---|---|---|---|---|---|---|
| Host Cell DNA [ng/ml] | | | | | | |
| % Reduction | | | | | | |
| pDADMAC [% w/v] | 0 | 0.0250 | 0.0375 | 0.0500 | 0.0750 | 0.0900 |
| Cell Culture 1 | 46500 | 3.9 | 3.1 | 0.2 | 0.2 | 0.2 |
| | 0 | 99.99 | 99.99 | 100 | 100 | 100 |
| Cell Culture 2 | 62900 | 59.9 | 16.0 | Not | 16.0 | 16.0 |
| | 0 | 99.91 | 99.98 | done | 99.98 | 99.98 |
| Cell Culture 3 | 45400 | 16.1 | 5.7 | 5.7 | 5.7 | 5.7 |
| | 0 | 99.96 | 99.99 | 99.99 | 99.99 | 99.99 |
| Cell Culture 4 | 44300 | 4.0 | 0.4 | 0 | 0.3 | 0.9 |
| | 0 | 99.99 | 100 | 100 | 100 | 100 |
| Cell Culture 5 | 51500 | 0.7 | 0.1 | 0.1 | 0.1 | 0.1 |
| | 0 | 100 | 100 | 100 | 100 | 100 |
| Cell Culture 6 | 50200 | 18.9 | 0.9 | 2.5 | 0.5 | 0.6 |
| | 0 | 99.96 | 100 | 100 | 100 | 100 |
| Mean Value % Red. | 0 | 99.97 | 99.97 | 100 | 100 | 100 |

The results in Table 4a confirm again the high potential of the cationic polymer pDADMAC on the flocculation of HCDNA. Already by the lowest concentration tested (0.025% w/v) an almost 100% reduction was obtained in all six cell cultures. The almost quantitative removal of HCDNA in an early step of downstream processing is very advantageous and disburdens the subsequent filtrations and capture chromatography.

The reduction of turbidity is the most important demand for the development of pre-cleaning steps. With several cell cultures expressing IgG1 or IgG2 antibodies (e.g. Bevacizumab, Trastuzumab, and Denosumab) turbidity arises in the concentrated solutions eluted from the capture chromatography column. It was observed in the experiments of this invention, that the reduction of turbidity in a pre-cleaning step prevents also the turbidity after capture chromatography, if the process steps are performed without interruption. No re-appearance of turbidity in the Protein A elution pools was observed.

TABLE 4b

Effect of pDADMAC concentration on reduction of turbidity in different cell culture batches
Turbidity [FNU]
% Reduction

| pDADMAC [% w/v] | 0 | 0.0250 | 0.0375 | 0.0500 | 0.0750 | 0.0900 |
|---|---|---|---|---|---|---|
| Cell Culture 1 | 28.10 | 22.80 | 8.53 | 5.57 | 2.92 | 2.85 |
|  | 0 | 18.86 | 69.64 | 80.18 | 89.61 | 89.86 |
| Cell Culture 2 | 19.90 | 10.30 | 3.20 | Not | 2.55 | 2.46 |
|  | 0 | 48.24 | 83.92 | done | 87.19 | 87.64 |
| Cell Culture 3 | 29.10 | 8.95 | 8.50 | 3.50 | 3.25 | 3.40 |
|  | 0 | 69.24 | 70.79 | 87.97 | 88.83 | 88.32 |
| Cell Culture 4 | 24.90 | 9.68 | 6.74 | 2.30 | 2.18 | 2.38 |
|  | 0 | 61.12 | 72.93 | 90.76 | 91.25 | 90.44 |
| Cell Culture 5 | 20.80 | 17.10 | 15.20 | 5.01 | 3.18 | 3.10 |
|  | 0 | 17.79 | 26.92 | 75.91 | 84.71 | 85.10 |
| Mean Value % Red. | 0 | 48.93 | 64.84 | 83.70 | 88.32 | 88.27 |

The results shown in Table 4b support the use of pDADMAC as flocculant. With 0.05% (w/v), the mean reduction in the cell cultures was above 80%. With a concentration of 0.075% (w/v), the mean reduction was about 88%. Higher concentrations (0.09% w/v) gave no further increase.

In another study the pDADMAC flocculation (without subsequent depth filtration) was evaluated for primary clarification of high-density cell culture feed streams. In contrast to the former experiments, the cell culture samples were aliquots of a selected 1000 L fermentation scale (cell density 9.3×10⁶ cells/ml), expressing Bevacizumab.

The experiments were performed according the following sequence of steps:
Collecting an aliquot of 40 ml from the fermentation broth (50 ml tubes)
Adding the flocculant in different concentrations
Incubation for 15 min at room temperature under gently stirring
Centrifugation at 3000 rpm/2000 g/5 min
Microfiltration (Millex Filter, 0.2 µm, EMD Millipore)
Immediate analysis of turbidity
Subsequent analysis for mab concentration, HCDNA, and HCP Table 5 summarizes the results of this study. The turbidity was measured in an instrument sold under the tradename HACH® Turbidimeter 2100Q and in contrast to the former experiments expressed as Nephelometric Turbidity Units (NTU). The instrument is measuring scattered light from the sample at a 90-degree angle from the incident white light.

TABLE 5

| Dose determination of pDADMAC | | | | | |
|---|---|---|---|---|---|
| pDADMAC [% w/v] | 0 | 0.0250 | 0.0375 | 0.0500 | 0.0750 | 0.1000 |
| pDADMAC [pg/cell] | 0 | 27 | 40.5 | 54 | 81 | 108 |
| mab conc. [mg/ml] | 1.14 | 1.14 | 1.15 | 1.15 | 1.12 | 1.20 |
| HCDNA [ng/mg] | 39500 | 3.61 | 1.54 | 0.58 | 0.49 | 1.76 |
| % Reduction | 0 | 99.99 | 100 | 100 | 100 | 100 |
| Turbidity [NTU] | 43.70 | 12.96 | 3.30 | 1.35 | 1.63 | 1.94 |
| % Reduction | 0 | 70.34 | 92.45 | 96.91 | 96.27 | 95.56 |
| HCP [µg/mg] | 2140 | 1960 | 1990 | 1970 | 1990 | 1820 |
| % Reduction | 0 | 8.41 | 7.01 | 7.94 | 7.01 | 14.95 |

The results shown in Table 5 confirm the previous findings for the reduction of HCDNA, turbidity and HCP (see Tables 1a, 2a, 4a, and 4b). The optimum dose of pDADMAC is defined as the minimal concentration of polymer that leads to a significant reduction in the turbidity of the supernatant. Adding higher concentrations of pDADMAC may not be beneficial. Higher concentrations may result in slightly lower turbidity level only (see Table 5, 0.1% w/v pDADMAC), or potentially lead to a slight reduction in the concentration of the product of interest in the supernatant (not observed until 0.1% w/v pDADMAC), or promote a faster return of turbidity (see Table 6). Higher concentrations may also lead to the generation of a population of smaller flocculates, which may break through the depth filters. The optimal pDADMAC concentration is in the range of 0.0375 to 0.075% (w/v). This refers to about 40 to 80 pg/cell under the conditions of this experiment. Within this range HCDNA reduction was 100%, the reduction of turbidity about 92-97%, and HCP reduction 7-8%. It has to be emphasized that the flocculation caused no detectable loss of mab.

A further experiment was performed with the same starting material as used for the experiments of Table 5, wherein the stability of turbidity after performing the flocculation, centrifugation and microfiltration was monitored. The same methods as described in Example 1 were applied. After flocculation with three concentrations of pDADMAC (0.0375% w/v, 0.075% w/v, and 0.09% w/v) the sterile filtered supernatant's turbidity was measured for a 24 hours period at room temperature. It turned out by parallel investigations, that centrifugation and microfiltration did not remove residual free pDADMAC. In contrast, chromatographic steps (e.g. Protein A) quantitatively removed the polymer. Table 6 shows the results of the stability experiments and the kinetic of re-appearance of turbidity.

TABLE 6

| Stability of filtered culture fluids after flocculation with pDADMAC Turbidity [FNU]/% Increase | | | |
|---|---|---|---|
| Time | pDADMAC concentration [% w/v] | | |
| [h] | 0.0375 | 0.0750 | 0.0900 |
| 0 | 5.48/0 | 3.09/0 | 3.65/0 |
| 1.5 | 6.09/11.1 | 3.16/2.3 | 4.64/27.1 |
| 3 | 6.85/25.0 | 3.91/26.5 | 6.49/77.8 |
| 8 | 6.95/26.8 | 7.41/139.8 | 11.9/126.0 |
| 24 | 8.12/48.2 | 14.7/375.7 | 21.5/489.0 |

Surprisingly, the turbidity level increased after three hours indicating ongoing precipitation. The effect strongly depends on the pDADMAC concentration. The increase of turbidity after 3 hours is 25% for 0.0375% (w/v) however about 78% for 0.09% (w/v). After 24 hours, the turbidity at the highest pDADMAC concentration reached non-flocculated (control) values (see Table 4b). The initial reduction on turbidity by flocculation was abolished.

From these results, it was concluded that 1) the flocculated and filtered supernatants require rapid further processing (depth filtration, Protein A chromatography) and 2) the lowest effective amount of pDADMAC has to be selected. Compared to 0.075% (w/v) the stability of 0.0375% (w/v) supernatants is much better with little increase up to 8 hours. This is an acceptable time window for routine production.

Example 4: Depth Filtration Experiments with and without Flocculation

When performing the flocculation with 0.0375-0.075% (w/v) pDADMAC in fermentation fluids of large scale (5,000 L) the cell separator, which then removes floc and cells, was highly loaded and post-run cleaning became rather time-consuming. This is also true for the fermenter, which has to be relieved from residual floc. Therefore, further experiments tested alternative pre-cleaning strategies to overcome this disadvantage.

Firstly, it was investigated if a flocculation step can be omitted and replaced by different set-ups of depth filters, including two-step depth filtration. Although several well-established filter systems including pre-filters were tested in many combinations, the results were not satisfying, i.e. the turbidity after cell separation and depth filtration remained at about 10 FNU and subsequent precipitation in the Protein A elution pools appeared with a turbidity of about 30 FNU for the best filter set-up. Furthermore, the depth filters did not reduce HCDNA and HCP.

Secondly, it was investigated if the separator after flocculation can be omitted when using just depth filters. Indeed, some of the filter set-ups clarified the flocculated cell culture fluid in a sufficient manner with an acceptable low flow-through turbidity (1-2 FNU). Although this strategy results in promising clearance, the required filter sizes and processing times are rather high and became a significant economic factor. This strategy was not pursued.

Example 5: Flocculation Experiments with Cell-Free Culture Supernatant

One preferred pre-cleaning strategy was elaborated in this example. The order of the pre-clean steps was as follows (see also FIG. 2B):

Harvest of cell culture fluid
Cell separation/centrifugation
Flocculation with pDADMAC (0.0375% w/v-0.075% w/v)

Depth filtration

Microfiltration (0.2 μm)

Protein A chromatography (MabSelect SuRe LX)

Compared to Examples 2 and 3 the flocculation was performed after cell separation/centrifugation and followed by depth filtration. This method was performed with 1 L, 10 L, 100 L and 5000 L culture fluid (Bevacizumab) and several parameters for the depth filtration were compared and optimized. The turbidity in the supernatants prior to flocculation was in the range of 30-100 FNU for the 5000 L scale.

The following types of depth filters were investigated:

PALL® Supercap 50 PDH4

PALL® Supercap 50 PDE2

PALL® Supercap 50 PDD1

PALL® Supercap 50 PEKM

PALL® Supercap 50 PEKX

3M BC25 90ZB08A

3M BV8 EMPHAZE® AEX hybrid purifyer

Again HCDNA, turbidity, HCP, and mab concentrations were analysed (methods see previous Examples) and from these results the PEKM, PDD1 and PDE2 are most suitable to clarify the flocculated supernatants at acceptable rates. Due to their double layer configuration, PDD1 and PDE2 showed more robust processing than PEKM (single layer) and therefore were the preferred depth filters for removal of floc. The flow through turbidity behind the depth filters was 1-2 FNU. The filtration time was 80 to 240 min at a load of 250-500 L/m². Both PDD1 and PDE2 filtrates showed only slight turbidity-growth in a period of 24 hours and both filtrates are considered stable enough for further processing on Protein A.

Conclusion: The flocculation with cell-free supernatant (after separation/centrifugation) turned out to be the preferred pre-cleaning strategy and well suitable for large-scale production of immunoglobulins. The flocculated supernatants, which had a turbidity of 30-100 FNU could be successfully processed by double layer depth filters, like PDD1 and PDE2. These type of filters can be loaded with at least 500 L/m². In case of supernatants with higher turbidity (>100 FNU), the effective filter area can be increased to avoid prolonged processing time. The finally selected pDADMAC concentration was 0.0375% (w/v), and is in full agreement with the small scale flocculation experiments in presence of cells and without the depth filtration (Examples 1-3).

Example 6: Flocculation of Cell Culture Supernatants with Higher IgG Concentration Using Different pDADMAC Concentrations (Table 7)

In this experiment two different small scale cell cultures were compared, accumulating different amounts of an IgG2 antibody (Denosumab). The culture volumes were 10 L and for the starting material two 10 L cultures were combined. The culture was harvested after 8 days and 10 days, respectively. The pooled 8 day culture had 3.86 mg/ml IgG, 42.4 μg/ml HCDNA, and 0.454 mg/ml HCP. The 10 day culture had 5.79 mg/ml IgG (+50%), 85. μg/ml HCDNA (+102%), and 0.506 mg/ml HCP (+11%). The cell culture supernatants were centrifuged (10 min at 4600 rpm) and flocculated (15 min incubation) as described in Example 1.

TABLE 7

Comparison of different starting materials on impurity reduction by pDADMAC flocculation

| pDADMAC [% w/v] | Culture 1/8 d/3.86 mg/ml IgG2 | | | Culture 2/10 d/5.79 mg/ml IgG2 | | |
|---|---|---|---|---|---|---|
| | HCDNA [ng/ml] (% red.) | HCP [μg/ml] (% red.) | Turbidity [FNU] (% red.) | HCDNA [ng/ml] (% red.) | HCP [μg/ml] (% red.) | Turbidity [FNU] (% red.) |
| 0.0000 | 40100 (0.00) | 424 (0.00) | 55.90 (0.00) | 80700 (0.00) | 525 (0.00) | 101.00 (0.00) |
| 0.0100 | 6150 (84.66) | 492 (−15.22) | 148.00 (−164.76) | 18600 (76.95) | 511 (2.67) | 238.00 (−135.64) |
| 0.0250 | 0.495 (100.00) | 427 (−0.71) | 2.02 (96.39) | 3.250 (100.00) | 469 (10.67) | 3.93 (96.11) |
| 0.0375 | 0.015 (100.00) | 365 (13.92) | 1.51 (97.30) | 0.091 (100.00) | 406 (22.67) | 2.29 (97.73) |
| 0.0750 | 0.011 (100.00) | 330 (22.17) | 1.54 (97.25) | 0.012 (100.00) | 376 (28.38) | 1.88 (98.14) |
| 0.0900 | 0.023 (100.00) | 354 (16.51) | 1.84 (96.71) | 0.028 (100.00) | 374 (28.76) | 1.98 (98.04) |
| 0.1000 | 0.035 (100.00) | 322 (24.06) | 1.89 (96.62) | 0.040 (100.00) | 378 (28.00) | 2.03 (97.99) |

Surprisingly, the two very different cultures behaved rather similar in the flocculation experiments. Again, the high potential of pDADMAC for removal of HCDNA was confirmed once more. Already by 0.025% pDADMAC the reduction of HCDNA was 100% (about 5 orders of magnitude). Looking at the turbidity, the reduction reaches 97-98% for 0.0375% and 0.075% pDADMAC. In this range, HCP was reduced by 22% and 28%, respectively. Surprisingly, the flocculation pre-clean strategy turned out to be rather robust with respect to the type of antibody, the cell density, and the mab titer. A culture-specific stoichiometric dosing is not necessary.

Example 7: Effect of Flocculation on Impurities after Affinity Capture with Protein A (Tables 8 to 10)

This example demonstrates the effect of flocculation on residual impurities in the Protein A elution pool. The starting materials were cell cultures expressing Trastuzumab (IgG1) in pilot scale (200 L, Table 8) and Bevacizumab in full scale (5000 L, Tables 9). The Protein A chromatography was performed as described in Example 8.2. The pDADMAC concentration was 0.0375% (w/v) and the depth filter was a filter sold under the tradename PALL® Supercap 50 PDE2.

TABLE 8

Reduction of impurities in Protein A eluates by preceding pDADMAC flocculation

| Pre-clean steps | HCDNA [pg/mg] (% Reduction) | HCP [ng/mg] (% Reduction) | Turbidity [FNU] (% Reduction) |
|---|---|---|---|
| Centrifugation + Depth filtration (control) | 889 (0) | 394 (0) | 42.9 (0) |
| Centrifugation + Flocculation + Depth filtration | 76 (91.5) | 204 (48.2) | 8.8 (79.5) |

The IgG concentrations in the Protein A eluates were 20.36 mg/ml for the non-flocculated control and 23.32 mg/ml for the flocculation process. In the control process no flocculation was performed and the supernatants after centrifugation were directly depth filtered and chromatographed over Protein A. The Protein A elution pools displayed significant precipitation in terms of turbidity of about 43 FNU in the control. In contrast, in the process with pDADMAC flocculation, the turbidity was strongly reduced by about 80%. The HCDNA was reduced by more than 90% to very low levels of 0.076 ppm, which is hardly detectable. Residual HCP was more prominent, i.e. 204 ppm, reflecting the 2-3 orders of magnitude higher load in the starter material. Its concentration was about halved compared to the control. These results clearly demonstrate the remarkable positive effect of pDADMAC flocculation on the product purity in Protein A eluates.

In the following Tables 9a and 9b routine in-process control data of two production batches (5000 L Bevacizumab) were shown to further demonstrate the surprisingly high reduction of impurities before and after Protein A chromatography. The Protein A chromatography was performed in two consecutive runs with 50% of the total volume in order to reduce the column volume of the costly resin. The subsequent incubations for virus inactivation were performed as described in Example 9.3

TABLE 9a

Large scale process with pDADMAC flocculation: HCDNA concentrations

| Step | Batch 1 IgG [mg/ml] | Batch 1 HCDNA [ng/mg] | Batch 2 IgG [mg/ml] | Batch 2 HCDNA [ng/mg] | Mean Value HCDNA [%] |
|---|---|---|---|---|---|
| Harvest | 1.5 | 87000 | 1.6 | 105250 | 100.0 |
| Centrifugation | 1.6 | 56500 | 1.6 | 57000 | 59.0 |
| Flocculation | 1.6 | n.d. | 1.6 | 150 | 0.16 |
| Filtration | 1.5 | n.d. | 1.5 | n.d. | 0.00 |
| Protein A (1)* | 16.9 | n.d. | 18.4 | n.d. | 0.00 |
| Protein A (2)* | 17.0 | n.d. | 18.4 | n.d. | |
| Inactivation (1) | 14.6 | n.d. | 14.5 | n.d. | 0.00 |
| Inactivation (2) | 15.0 | n.d. | 15.1 | n.d. | |

*The Protein A chromatography was performed in two consecutive runs with a 50% portion each of the total volume
n.d. := not detectable, below detection limit of the test method TABLE 9b Large scale process with pDADMAC flocculation: HCP concentrations

| Step | Batch 1 IgG [mg/ml] | Batch 1 HCP [ug/mg] | Batch 2 IgG [mg/ml] | Batch 2 HCP [ug/mg] | Mean Value HCP [%] |
|---|---|---|---|---|---|
| Harvest | 1.5 | 778.1 | 1.6 | 871.4 | 100.0 |
| Centrifugation | 1.6 | 839.0 | 1.6 | 921.9 | 106.8 |
| Flocculation | 1.6 | 740.4 | 1.6 | 811.2 | 94.1 |
| Filtration | 1.5 | 662.2 | 1.5 | 744.9 | 85.3 |
| Protein A (1)* | 16.9 | 0.269 | 18.4 | 0.252 | 0.028 |
| Protein A (2)* | 17.0 | 0.255 | 18.4 | 0.160 | |
| Inactivation (1) | 14.6 | 0.259 | 14.5 | 0.225 | 0.027 |
| Inactivation (2) | 15.0 | 0.270 | 15.1 | 0.152 | |

HCDNA was hardly detectable already after flocculation and below the detection limit in the subsequent steps (Table 9a). Flocculation and depth filtration reduced the HCP only by about 15% (Table 9b). However, the Protein A chromatography, due to its high selectivity for IgG-Fc, reduced the HCP impurities by more than 99.9%. Nevertheless, the residual HCP concentrations of 160-270 ppm after Protein A chromatography indicate the need for further polishing steps, at least in case of a therapeutic antibody for human use.

Table 10: Comparison of Leached Protein A for Different Processes

In the experiments underlying Table 10 three different processes were compared for leached Protein A in the Protein A elution pools. Process C is the process according this invention making use of pDADMAC flocculation under the same condition as described in Example 7/Table 8 (200 L Trastuzumab). The results of two runs were compared with a previously established process (Process B) utilizing anion exchange flow through chromatography (Nuvia Q) preceding the Protein A step. Process A is a further control without a pre-cleaning step (except centrifugation and filtration). Processes A and B are described in WO2015135884. All processes were performed at room temperature. The Protein A chromatography was performed as described in Example 8.2.

| Process | Pre-Cleaning Step | Leached Protein A in Protein A elution pool | | |
|---|---|---|---|---|
| | | Run 1 [ng/mg] | Run 2 [ng/mg] | Mean Value [%] |
| A | None | 25.1 | 21.6 | 100 |
| B | Nuvia Q Flow Through | 10.3 | 7.8 | 39 |
| C | pDADMAC Flocculation | 5.8 | 3.8 | 21 |

Process A: Cell separation → Depth Filtration → Microfiltration → Protein A
Process B: Cell separation → Depth Filtration → Microfiltration → Anion exchange chromatography (Nuvia Q, flow through) → Protein A (as described in WO2015135884)
Process C: Cell separation → Flocculation (pDADMAC) → Depth Filtration → Microfiltration → Protein A The leached Protein A with Process C was significantly lower than with Process B which was already a valuable improvement to lower leached Protein A compared to the control Process A. Reduction of leached Protein in Process C was about 48% compared to Process B and about 79% compared to Process A. Therefore, besides the prominent reduction of HCDNA and turbidity, pDADMAC flocculation additionally reduces leached Protein A to a remarkable extent.

Example 8: Downstream Process-Purification of Immunoglobulin from Pre-Cleaned Culture Supernatants In the following methods are described which were developed in small scale and at first applied for a 100 L pilot scale process of Bevacizumab (IgG1). The same process, with few adaptions only, was later on successfully scaled up to 5000 L. After further slight adaptions, this process was also established for Trastuzumab (IgG1) and Densosumab (IgG2).

Example 8.1: Selection of Chromatography Resins (Table 11)

Subsequent to an extended screening of commonly used chromatographic media for capture, intermediate and polishing steps, which was disclosed in WO2015135884, the following chromatography resins were selected for the downstream process of immunoglobulins (Table 11):

TABLE 11

| Preferred chromatography resins | | | | |
|---|---|---|---|---|
| Process Step | Resin | Type | Ligand | Supplier |
| Capture | MabSelect SuRe LX | Affinity | Alkali-stabilized Protein A derivative | GE Healthcare |
| Intermediate | Poros 50 HS | CEX | Sulfopropyl (SP) | Applied Biosystems |
| Polishing | Capto Q | AEX | Trimethylammonium | GE Healthcare |
| Polishing | CaptoAdhere | MMC | N-Benzyl-N-methyl ethanol amine | GE Healthcare |

CEX = Cation exchange chromatography;
AEX = Anion exchange chromatography;
MMC = Mixed-mode chromatography The chromatographic runs were performed with an Äkta Purifier System (GE Healthcare) at room temperature.

Example 8.2: Protein A Chromatography

The Protein A capture chromatography was performed with resin sold under the tradename MABSELECT SURE® LX (Table 11). The sample was taken after depth filtration and microfiltration of the flocculated supernatant as described in Example 5. The column dimension was 20 cm diameter×10.4 cm bed height (packed volume about 3.3 L). The Protein A column was equilibrated with 20 mM Tris-acetate buffer, pH 7.2. The product solution (about 49.5 L) was loaded with 15.8 to 40.6 protein/L resin. The column was washed with equilibration buffer (2 CV), followed by 40 mM Na-phosphate, 1.5 M NaCl, 2 M urea, 10 mM EDTA, pH 7.4. The elution was performed with 100 mM Na-citrate, pH 3.5. The flow rates were 210 cm/h. The regeneration of the MABSELECT SURE® LX resin was performed by washing in reverse direction consecutively with (i) 0.2 M NaOH (2 CV), (ii) WFI (2 CV), 3.5% acetic acid, 100 mM Na-sulphate (2 CV) and (iii) WFI (2 CV). The column was re-equilibrated for the next run or stored in 20% ethanol. The yields were between 94-98%.

Example 8.3: Virus Inactivation

As shown in the FIGS. 1 and 2, a viral inactivation step takes place after the Protein A affinity chromatography. Advantage is taken of the low pH elution from the affinity matrix. In such an aqueous acid environment many viruses, especially those of the enveloped type, are instable and disintegrate. The Protein A method developed for this invention produces an eluate having a pH of 3.5 (see Example 8.2.). The monoclonal antibody was eluted from the Protein A column in 100 mM Na-citrate buffer, pH 3.5 directly into the virus inactivation tank A. The eluate was diluted about 2-fold by WFI directly in the tank A. The pH of the solution was controlled and re-adjusted to 3.5 with 100 mM citric acid, if necessary, and the solution was subsequently transferred to the virus inactivation tank B, where it was agitated with 65 rpm at a temperature of 20-24° C. for 60 minutes. Then the pH of the solution was adjusted to pH 4.5 with 100 mM NaOH, providing the starting condition for the subsequent cation exchange chromatography step.

Example 8.4: Cation Exchange Chromatography with Poros 50 HS

Separation of contaminants such as HCP and leached Protein A, and product-related substances such as charge variants and aggregates was performed by strong cation exchange chromatography with sulfopropyl (SP) ligands (Table 11) used as an intermediate step. The packed column with resin sold under the tradename POROS® 50 HS (dimension=14 cm diameter×41 cm bed height, packed volume about 6.3 L) was equilibrated consecutively by (i) WFI (water for injection, 2 CV) and (ii) 20 mM Na-citrate, pH 4.9 (2 CV). The product solution obtained after the virus inactivation and the sample adjustments (pH 4.5) as described in Example 8.3 was loaded onto the column with about 7.3 to 17.1 g protein/L resin, thereby passing a 0.45 μm Kleenpak Nova pre-filter (Pall Corporation). The column was washed with WFI (1 CV) and equilibration buffer (2 CV) before a gradient elution followed. The gradient consists of two parts with different slopes. The gradient was formed by mixing 20 mM Na-citrate, pH 4.9 (buffer A) and 40 mM Na-phosphate, pH 7.2 (buffer B) in the following ratios and sequence: (i) 100% A (0.2 CV), (ii) linear gradient to 40% A+60% B (2 CV) (iii) linear gradient to 100% B (10 CV); (iv) 100% B (2 CV). The flow rates were 75 cm/h during the gradient, otherwise 150 cm/h. The eluate was separated in fractions to allow specific pooling. Collection of fractions during gradient elution started when $A_{280}$ raised a value >0.1 AU. Fraction volume was about 2 L. In total, about 20 fractions were collected. The regeneration of the POROS® 50 HS resin was performed by washing consecutively with (i) 1 M NaCl (2 CV) and (ii) 1M NaOH (2 CV). The column was afterwards stored in 10 mM NaOH. The yield in the selected pool was about 62-68% due to the depletion of a significant amount of product-related impurities.

Example 8.5: Mixed-Mode Chromatography with CAPTO®Adhere

The final polishing step was performed with the mixed mode resin sold under the tradename CAPTO®Adhere, which makes use of the ligand N-benzyl-N-methyl ethanolamine (Table 11). The ligand bears positively charged groups and therefore provides beside hydrophobic interactions also anion exchanger functions. The chromatography is able to reduce the remaining traces of contaminants, such as HCDNA, HCP and basic charge variants. Residual leached Protein A, product aggregates and product fragments can also be removed by this step. The CAPTO®Adhere polishing step was performed in binding mode, which offers the advantage of a buffer exchange into the selected final buffer.

The pH of the Poros 50 HS pool obtained subsequent to the procedures described in Example 8.4 was adjusted to pH 7.2 by adding 100 mM NaOH. The size of the packed column was 14 cm diameter×23 cm bed height (packed volume about 3.5 L). The resin was equilibrated with 50.48 mM Na-phosphate, pH 7.2 (3 CV). The product solution was loaded onto the column with 6.3 to 17.8 g protein/L resin) followed by equilibration buffer (3 CV). The elution was performed with 50.48 mM Na-phosphate, pH 5.0. The flow rate was 240 cm/h. The yield ranged from 87 to 98%. The column was regenerated with 2 M NaCl+100 mM citric acid (2 CV) and 1 M NaOH (2 CV) in reverse flow.

Example 8.6: Anion Exchange Chromatography with CAPTO® Q

Instead of mixed-mode chromatography, anion exchange chromatography using chromatograph products sold under the tradename CAPTO® Q was performed as the final polishing step in this example. The anion exchange chromatography was performed in flow through mode. Prior to column load the pooled fractions of the cation exchange chromatography underwent pH adaption with acetic acid to pH 8.0. The CAPTO® Q column was equilibrated with 25 mM Tris puffer, pH 8.0. After sample load the chromatography was performed with the same buffer. The immunoglobulin did not bind to the chromatography resin and was obtained in the flow through.

Example 8.7: Virus Filtration

Nanofiltration constitutes the final virus clearance step and the most demanding and most reliable virus removal method operating on the basis of size exclusion in the nanometer range. The virus filtration was placed directly after the mixed mode chromatography using the CAPTO®Adhere elution pool of Example 8.5 or the CAPTO® Q flow through pool of Example 8.6 after pH adaption to 6.2 with Na-phosphate or to pH 5.0 with acetic acid. The virus removal filtration was performed at room temperature with a filtration device sold under the tradename VIRESOLVE® Pro Modus 1.1 (EMD Millipore) using a diaphragm pump sold under the tradename QUATTRO-FLOW®. A filter sold under the tradename OPTICAP® XL 150 PES (EMD Millipore) with 0.1 μm pore size was placed before the virus filter in order to avoid clogging of the virus filter by aggregates. The filters were conditioned with 1.5 L of formulation buffer, e.g. 50.48 mM Na-phosphate buffer pH 6.2 or 18 mM Na-acetate buffer pH 5.2. Pressure set point was 2±0.2 bar during the filtration process. Following the load with about 500-600 L/m² a volume of about 0.5-1 L of formulation buffer, e.g. 50.48 mM Na-phosphate buffer pH 6.2 was used to wash out residual mab from the filter train. Virus filter was integrity tested with 3.4 bar pressure and a 1 min test duration.

Example 8.8: Tangential Flow Ultrafiltration/Diafiltration (TF-UF/DF)

The role of the final ultrafiltration/diafiltration step is to adjust the concentration of the protein solution and if required to perform a buffer exchange into the drug product bulk formulation. In case the final polishing step was a mixed-mode chromatography in binding mode a buffer exchange was already performed on the level of the mixed-mode chromatography enabled by the binding mode (see Example 8.5). Furthermore, besides the buffer, other ingredients of the final bulk formulation such as surfactants, stabilizers and/or cryopreservants can be introduced via diafiltration. Alternatively, the concentrated mab solution is supplemented directly with these substances.

The nanofiltered product solution of Example 8.7. was collected in the tank of the UF/DF skid and was concentrated to about 40+/−2 g/L using Omega Centrasette membrane cassette (Pall Corporation, 30 kD cutoff). Feed pressure was provided with a diaphragm pump sold under the tradename QUATTROFLOW® 150. Transmembrane pressure was set to 1 bar and feed and retentate pressure were 1.0 and 0.6 bar, respectively. There was no loss of mab during this step. The concentrated product solution was supplemented with Polysorbate 20 and trehaloseor sorbitol. The final bulk concentration of the mab was adjusted for example to 30+/−2 g/L or to 80+/−5 g/L. A final microfiltration (sterile filtration) was performed with a 0.2 μm Mini Kleenpak filter capsule (Pall Corporation).

LIST OF REFERENCES

1. R. L. Fahrner et al., 2001 "Industrial Purification of Pharmaceutical Antibodies: Development, Operation, and Validation of Chromatography Processes", Biotechnology and Genetic Engineering Reviews 18, 301-327

2. S. S. Farid, 2009 "Economic Drivers and Trade-Offs in Antibody Purification Processes: The future of therapeutic MAbs lies in the development of economically feasible downstream processes", BioPharm Int. Supplements, Oct. 2, 2009

3. M. Felo et al., 2015 "Industrial application of impurity flocculation to streamline antibody purification processes" Pharm. Bioprocess 3(2), 115-125

4. P. Gagnon, 1996 "Purification Tools for Monoclonal Antibodies", Validated Biosystems, Inc., 1-253

5. V. G. Kadajji and G. V. Betageri, 2011 "Water Soluble Polymers for Pharmaceutical Applications", Polymers 3, 1972-2009

6. Y (K) Kang et al., 2013 "Development of a Novel and Efficient Cell Culture Flocculation Process Using a Stimulus Responsive Polymer to Streamline Antibody Purification Processes", Biotechnol. Bioeng. 110(11), 2928-2937

7. B. Kelly et al., 2009 "Downstream processing of monoclonal antibodies: Current practices and future opportunities", in: Process Scale Purification of Antibodies, edited by U. Gottschalk, John Wiley & Sons, Inc.

8. H. F. Liu, 2010 "Recovery and purification process development for monoclonal antibody production", mabs Landes Biosciences 2(5), 480-499

9. H. Luo et al., 2017 "Liquid-liquid phase separation causes high turbidity and pressure during low pH elution process in Protein A chromatography", J. Chromatogr. A, 1488, 57-67.

10. T. McNerney et al., 2015, "PDADMAC flocculation of Chinese hamster ovary cells: Enabling a centrifuge-less harvest process for monoclonal antibodies" mAb (Amgen) 7(2), 413-427

11. A. A. Shukla et al., 2005, "Strategies To Address Aggregation During Protein A Chromatography" BioProcess International, May 2005, 36-44.

12. N. Singh et al., 2016, "Clarification Technologies for Monoclonal Antibody Manufacturing Processes: Current State and Future Perspectives", Eur. J. Biochem. 192, 767-775

13. WO03002713
14. WO2001150110
15. WO2007035283
16. WO2008091740
17. WO2008127305
18. WO2010151632
19. WO2011146394
20. WO2013090820
21. WO2014004281
22. WO2014133459
23. WO2014196926
24. WO2015130222
25. WO2015135884
26. WO2016153983
27. WO2017217930
28. WO9216553
29. WO9222653
30. WO9411026
31. WO9522389
32. WO9729131
33. WO9845331

The invention claimed is:

1. A method for prevention of precipitations in the course of a capture affinity chromatography of an immunoglobulin from a cell culture fluid, the method comprising the following steps in the following order:

(a) adding a flocculation-inducing compound to the cell culture fluid;

(b) depth filtration of the mixture of step (a);

(c) exposing the filtrate obtained in step (b) to affinity chromatography, wherein the immunoglobulin is bound to the affinity chromatography medium;

(d) washing the affinity chromatography medium by adding a washing buffer with a pH value of 5 to 9 and a ionic strength of 0.1 to 5.0 mol/L to the affinity chromatography medium of step (c); and (e) eluting the immunoglobulin from the affinity chromatography resin by adding an elution buffer with a pH value of 2.5 to 4.5 to the affinity chromatography medium, wherein the flocculation-inducing compound is poly (diallyldimethylammonium chloride) and wherein except the poly (diallyldimethylammonium chloride) no further substances are added for performing the flocculation, wherein the method is carried out at large scale, in which the immunoglobulin eluted from the column of the capture step amounts to more than 50 g.

2. The method of claim 1 wherein step (a) comprises the following steps:

(a1) centrifugation and/or filtration of the cell culture fluid; and (a2) adding a flocculation-inducing compound to the supernatant or filtrate obtained in step (a1).

3. The method of claim 1, wherein the poly (diallyldimethylammonium chloride) has a molecular mass of 10 kDa to 10 000 kDa.

4. The method of claim 1, wherein the poly (diallyldimethylammonium chloride) is added in a final concentration of 0.01 to 1.0% (w/v).

5. The method of claim 1, wherein the flocculation with poly (diallyldimethylammonium chloride) is performed without further adjustment of pH or conductivity.

6. The method of claim 1, wherein the affinity chromatography is a Protein A chromatography.

7. The method of claim 1, wherein between step (b) and (c) microfiltration is carried out.

8. The method of claim 1, wherein step (c) is carried out at most 8 h after step (b).

9. The method of claim 1, wherein the immunoglobulin is IgG1 or IgG2.

10. A method for purifying an immunoglobulin, comprising the steps as defined in claim 1 and comprising one or more further steps following the affinity chromatography wherein the one or more further steps are selected from the group consisting of virus inactivation, anion exchange chromatography, cation exchange chromatography, mixed-mode chromatography, nanofiltration, and ultrafiltration/diafiltration.

11. The method according to claim 10, wherein the one or more further steps comprise: (f) incubating the eluate of step (e) for virus inactivation at a low pH value of 2.5 to 4.5, for at least 10 minutes.

12. The method according to claim 10, wherein the one or more further steps comprise:

(f) incubating the eluate of step (e) for virus inactivation at a low pH value of 2.5 to 4.5, for at least 10 minutes;

(g) performing a cation exchange chromatography;

(h) performing a mixed-mode chromatography or an anion exchange chromatography;

(i) exposing the eluate of step (h) to nanofiltration, optionally wherein the eluate of step (h) is exposed to one or more further processing steps prior to nanofiltration; and (j) exposing the filtrate of step (i) to ultrafiltration/diafiltration, optionally wherein the filtrate of step (i) is exposed to one or more further processing steps prior to the ultrafiltration/diafiltration.

13. The method according to claim 12, wherein the cation exchange chromatography (g) is performed in a bind-elute mode, optionally including one or more washing steps.

14. The method according to claim 12, wherein the mixed mode chromatography in step (h) is performed in a bind-elute mode, optionally including one or more washing steps.

15. The method according to claim 12, wherein the chromatography (h) is performed in flow through mode.

16. The method according to claim 12, wherein the cation exchange chromatography of step (g) is performed with sulfopropyl ($—CH_2CH_2CH_2SO_3—$) as a ligand.

17. The method according claim 12, wherein the mixed-mode chromatography medium of step (h) is performed with a positively charged mixed-mode medium.

18. The method of claim 2, wherein the flocculation-inducing compound is a cationic compound selected from the group consisting of a divalent metal ion salt, a water-soluble organic polymer, and a water-insoluble organic polymer.

19. The method of claim 18, wherein the water-soluble organic polymer is poly (diallyldimethylammonium chloride).

20. The method of claim 19, wherein the poly (diallyldimethylammonium chloride) has a molecular mass of 10 kDa to 10 000 kDa.

21. The method of claim 19, wherein the poly (diallyldimethylammonium chloride) is added in a final concentration of 0.01 to 1.0% (w/v).

22. The method of claim 19, wherein except the poly (diallyldimethylammonium chloride) no further substances are added for performing the flocculation.

23. The method of claim 19, wherein the flocculation with poly (diallyldimethylammonium chloride) is performed without further adjustment of pH or conductivity.

24. The method of claim 8, wherein step (c) is carried out at most 3 h after step (b).

25. The method according to claim 12, wherein the cation exchange chromatography of step (g) is performed with a medium comprising sulfopropyl ($—CH_2CH_2CH_2SO_3—$) as a ligand.

26. The method according to claim 12, wherein the mixed-mode chromatography medium of step (h) is performed with a positively charged mixed-mode medium, comprising N-benzyl-N-methyl ethanolamine as a ligand, bound to a cross-linked agarose matrix.

* * * * *